(12) United States Patent
Burdet et al.

(10) Patent No.: US 6,348,606 B2
(45) Date of Patent: Feb. 19, 2002

(54) CYCLIC DIENOL ETHERS

(75) Inventors: Bruno Burdet, Baldersheim (FR);
August Rüttimann, Arlesheim (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/764,016

(22) Filed: Jan. 17, 2001

Related U.S. Application Data

(62) Division of application No. 09/368,046, filed on Aug. 3, 1999, now Pat. No. 6,201,155.

(30) Foreign Application Priority Data

Aug. 5, 1998 (EP) .............................. 98114684
Jun. 28, 1999 (EP) .............................. 99112340

(51) Int. Cl.[7] ...................... C07D 317/08; C07C 43/30
(52) U.S. Cl. ...................... 549/434; 549/369; 549/430; 568/591; 568/667; 568/670
(58) Field of Search ................. 568/591, 667, 568/670; 549/430, 434, 369

(56) References Cited

U.S. PATENT DOCUMENTS

| | | | |
|---|---|---|---|
| 4,157,345 A | 6/1979 | Rosenberger | 260/586 R |
| 5,210,314 A | 5/1993 | Ernst et al. | 568/345 |
| 5,225,604 A | 7/1993 | Moldt | 568/347 |
| 5,654,488 A | 8/1997 | Krause et al. | 568/345 |

FOREIGN PATENT DOCUMENTS

| EP | 0 816 334 A1 | 1/1998 |
|---|---|---|

OTHER PUBLICATIONS

N. Nazarov, et al., "Condensation of Acetals with 1–Ethoxydienes," *J. Gen. Chem. USSR*, vol. 28, pp. 2477–2483 (1958).

S. M. Makin, et al., "The Chemistry of Unsaturated Ethers: VII. Addition of the Acetal of β–C14–Aldehyde to 1–Ethoxoy–Methyl–1,3–Butadiene, A new Synthesis of β–C19–Aldehyde," *Gen. Chem. USSR*, vol. 31, pp. 3096–3099 (1961).

S. M. Makin, et al., "Chemistry of Unsaturated Ethers: XVI. Telomerization of 1–Alkoxy–1,3–Dienes with Acetals of Unsaturated Aldehydes," *J. Gen. Chem. USSR*, vol. 32,pp. 3112–3114 (1962).

Akihiko Ishida, et al., "A New Method for the Preparation of δ–Alkoxy–α, β–unsaturated Aldehydes and Polyenals," *Bull. Chem. Soc. Jap.*, vol. 50 (5), pp. 1161–1168 (1977).

Ian Fleming and Thomas V. Lee, "The γ–Alkylation of Enones using Silyl Dienol Ethers: The Effect of Changing the Electrophile and of Changing the Silyl Group," *Tetr. Lett.* vol. 22, pp. 705–708 (1981).

Derwent English language abstract of EP 0 816 334 (1998).

*Primary Examiner*—Sreeni Padmanabhan
(74) *Attorney, Agent, or Firm*—Bryan Cave LLP

(57) ABSTRACT

The claimed invention relates to cyclic dienol ethers of formula (III).

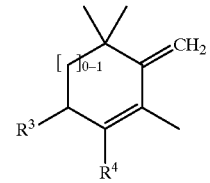

wherein $R^3$ is hydrogen and $R^4$ is $C_{1-4}$ alkoxy or $R^3$ and $R^4$ together form an optionally substituted methylenedioxy group —O—C($R^5$)($R^6$)—O—, wherein $R^5$ and $R^6$ are each independently hydrogen, $C_{1-4}$ alkyl or phenyl.

6 Claims, No Drawings

CYCLIC DIENOL ETHERS

This is a divisional of U.S. application Ser. No. 09/368,046, filed Aug. 3, 1999 is now U.S. Pat. No. 6,201,155.

FIELD OF THE INVENTION

The present invention is concerned with a novel process for the manufacture of symmetrical, terminally ring-substituted polyenes, especially carotenoids of the canthaxanthin, astaxanthin, etc., types and the corresponding 2,2'-dinor-carotenoids (generally referred to as 4,4'-diketo-carotenoids) from acetalized polyene dialdehydes by an acid-catalyzed condensation reaction with cyclic dienol ethers.

BACKGROUND OF THE INVENTION

Lewis acid-catalyzed additions of $\alpha,\beta$-unsaturated ethers (aldehyde enol ethers) to acetals are known and date back to the work of Muller-Cunradi and Pieroh (see U.S. Pat. No. 2,165,962). Hoaglin and Hirsch [J.A.C.S. 71, 3468 et seq. (1949)] investigated this reaction further and broadened the possible applications, which Isler et al. likewise did in the nineteen fifties with respect to the synthesis of β-carotene, crocetin dialdehyde, lycopene, as well as, β-apocarotenoids [Helv. Chim. Acta 39, 249 et seq. and 463 et seq. (1956), ibid. 42, 854 et seq. (1959) and U.S. Pat. Nos. 2,827,481 and 2,827,482]. Later, Mukaiyama [Angew. Chem. 89, 858 et seq. (1977) and Org. Reactions 28, 203 et seq. (1982)] extended the reaction by using the readily accessible trimethylsilyl enol ethers.

Also enol ethers of aliphatic and alicyclic ketones, including alkyl enol ethers and silyl enol ethers, react with acetals to give β-alkoxy-ketones or, with cleavage of alcohol, to give the corresponding elimination products [Chem. Lett. 1974, 16 et seq., J.A.C.S. 102, 3248 et seq. (1980), Chem. Lett. 1987, 1051 et seq. as well as ibid., 1975, 569 et seq.].

The first Lewis acid-catalyzed condensations of 1-alkoxy-1,3-dienes (dienol ethers) with $\alpha,\beta$-unsaturated acetals were reported by Nazarov and Krasnaya [J. Gen. Chem. USSR 28, 2477 et seq. (1958)] and by Makin [Pure & Appl. Chem. 47, 173 et seq. (1976), J. Gen. Chem. USSR 31, 3096 et seq. (1961) and 32, 3112 et seq. (1962)]. Here, the coupling of the acetal to the dienol ether takes place as far as can be seen exclusively at its γ-position with the formation of a chain-lengthened $\alpha,\beta$-unsaturated acetal, which, however, in competition with the first acetal reacts with further dienol ether with the formation of a Pa/27.7.1999 further, chain-lengthened ($\alpha,\beta$-unsaturated acetal, etc. [telomer formation; see also Chemla et al., Bull. Soc. Chim. Fr. 130, 200 et seq. (1993)]. For this reason such a condensation has been found not to be workable for synthetic purposes, especially for the synthesis of apocarotenals [Isler et al., Adv. Org. Chem. 4, 115 et seq. (1963)].

1-Alkoxy-1,3-dienes and trimethylsilyloxydienes [of the $CH_2$=CH—CH=CH—$OSi(CH_3)_3$-type] can be condensed with $\alpha,\beta$-unsaturated acetals in the presence of Lewis acid catalysts, as disclosed by Mukaiyama et al. in Chem. Lett. 1975, 319 et seq. In this coupling, the attack also seems to take place exclusively at the terminal (γ) carbon atom of the diene system ["γ-attack"; Mukaiyama et al., Bull. Chem. Soc. Japan 50, 1161 et seq. (1977) and Japanese Patent Publication (Kokai) 36,645/1977/Chem. Abs. 87, 201825 t, (1977)]. In contrast to the reaction with 1-alkoxy-1,3-dienes, in which an $\alpha,\beta$-unsaturated acetal results, the reaction of trimethylsilyloxydienes with acetals forms an aldehyde that does not react further with the diene (no telomer formation). Thereby, zinc bromide and many other Lewis acids are required as catalysts only in small amounts [Fleming (et al.), Tetr. Lett. 1979, 3209 et seq. and Chimia 34, 265 et seq. (1980) as well as Brownbridge, Synth. 1983, 85 et seq]. By using this method, Mukaiyama et al. were able to synthesize vitamin A [Kokai 36,645/1977, Chem. Lett. 1975, 1201 et seq. and Bull. Chem. Soc. Japan 51, 2077 et seq. (1978)] and workers from Rhône-Poulenc developed new routes to carotenoids and vitamin A [German Patent Publication, i.e., Deutsche Offenlegungsschrift (DOS), 2,701,489 and A.E.C. Sociétéde Chimie Organique et Biologique No. 7824350].

The aforementioned Lewis acid-catalyzed condensation of a dienol ether with an $\alpha,\beta$-unsaturated acetal based on the work of Nazarov and Krasnaya, Makin, and Chemla et al. would be a very valuable access to apocarotenals and bis-apocarotenals if the yield of the desired primary product of the . . . CH=CH—CH($Oalkyl^1$)—$CH_2$—CH=CH—CH($Oalkyl^1$)($Oalkyl^2$)-type could be increased and the telomer formation could be suppressed. Thus, the desired polyene aldehyde of the . . . CH=CH—CH=CH—CH=CH—CHO-type could be obtained from this primary product by hydrolysis of the acetal group C($Oalkyl^1$)($Oalkyl^2$) and elimination of $alkyl^1OH$ [European Patent Publication (EP) 0 816 334 A1].

Some examples are known wherein ketone dienol ethers of the . . . CH=CH—CH=C(O alkyl/trimethylsilyl)-$CH_2$-alkyl-type are reacted with aldehydes, acetals, orthoesters and other electrophiles to give $\alpha,\beta$-unsaturated ketones of the . . . E—$CH_2$ —H=CH—CO—$CH_2$-alkyl-type (E represents an electrophilic substrate) [Tetr. Lett. 22, 705 et seq. and 2833 et seq. (1981), ibid., 27, 2703 et seq. (1986), ibid. 29, 685 et seq. (1988) as well as Chem. Ber. 123, 1571 et seq. (1990)]. The usefulness of this reaction appears to be somewhat limited, not on reactivity grounds, but because of the difficult accessibility of the aforementioned ketone dienol ethers, because, inter alia, regioselectivity problems have to be taken into consideration in their production [formation of the undesired regioisomers of the . . . $CH_2$—CH=CH—C(O-alkyl/trimethylsilyl)=CH-alkyl-type].

Based on the aforementioned dienol ether condensation, A. Rüttimann has recently developed a novel, economical synthesis of apocarotenals and bis-apocarotenals (EP 0 816 334 A1) that is advantageous because the C—C linkage is effected under catalytic conditions, namely using a Lewis acid catalyst. Moreover, no phosphorus- or sulphur-containing reagents are required in this approach.

SUMMARY OF THE INVENTION

A novel synthesis of canthaxanthin, astaxanthin, the corresponding 2,2'-dinor-carotenoids and structurally similar, symmetrical carotenoids having two terminal rings (4,4'-diketo-carotenoids) has now been found. This novel synthesis is likewise based on a catalyzed dienol ether condensation and also avoids the use of phosphorus- and sulphur-containing reagents, but makes use in a very refined and surprising manner of a cyclic compound as a reaction participant that has not only the main features of the terminal ring, but also the dienol ether grouping required for the condensation.

An object of the present invention is to manufacture the aforementioned symmetrical carotenoids starting from polyene diacetals while avoiding, as much as possible, the aforementioned disadvantages of the state of the art and replacing the Wittig, Horner or Julia reaction hitherto used for this purpose. This object is achieved in accordance with the invention by reacting a polyene diacetal with a cyclic dienol ether in the presence of a suitable catalyst, namely a Lewis acid or Brönsted acid, and, after hydrolyzing the resulting condensation product, undertaking a base- or acid-induced elimination of alcohol at the two ends of the mainly conjugated hydrocarbon chain bonded to the two rings in order to obtain the desired symmetrical, terminally ring-substituted fully conjugated polyene. Not only is the reaction of the cyclic dienol ether with the polyene diacetal novel, but, surprisingly, it is effected with an exclusive attack of the acetal at the γ-position of the dienol ether. By the base- or acid-induced elimination of the alkanol subsequent to the hydrolysis, two conjugated C—C double bonds are formed without the need for a phosphorus- or sulphur-containing reagent, which is in contrast to the methodology hitherto usually employed in this field.

Accordingly, the present invention is concerned with a process for the manufacture of a symmetrical, terminally ring-substituted polyene of formula I

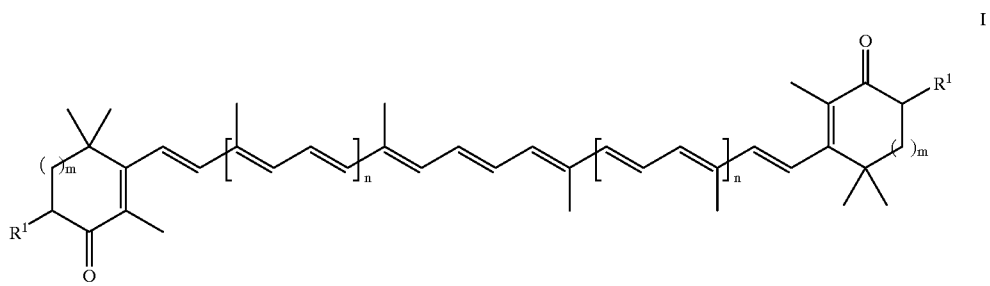

wherein
$R^1$ is hydrogen or hydroxy;
m is 0 or 1; and
n is 0, 1, or 2
which comprises reacting a polyene di(O,O-dialkyl acetal) of formula II

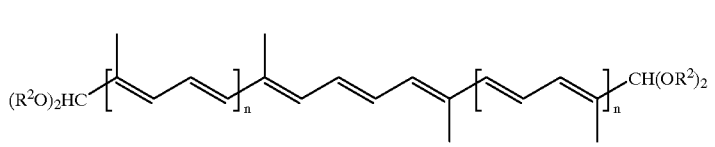

wherein
$R^2$ is $C_{1-6}$-alkyl and
n is as defined above,
with a cyclic dienol ether of formula III

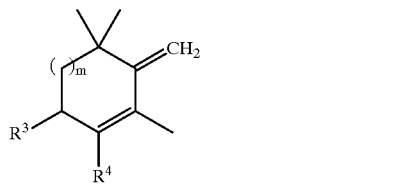

wherein
$R^3$ is hydrogen;
$R^4$ is $C_{1-4}$-alkoxy, or
$R^3$ and $R^4$ together form an optionally substituted methylenedioxy group, —O—C($R^5$)($R^6$)—O—, wherein $R^5$ and $R^6$ are each independently hydrogen, $C_{1-4}$-alkyl or phenyl, and
m is defined as above
in the presence of a Lewis or Brönsted acid, and hydrolyzing the reaction product under acidic conditions and cleaving off the alkanol $R^2OH$ from the thus-obtained compound of formula IV

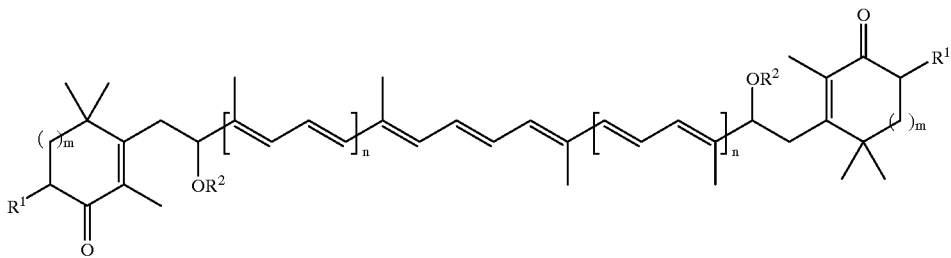

IV wherein
  $R^1$ is hydrogen or hydroxy, depending on whether $R^3$ and $R^4$ in formula III each are hydrogen or $C_{1-4}$-alkoxy or together signify the optionally substituted methylenedioxy group, and
  $R^2$, m and n have the significances given above,
under basic or acidic conditions.

Additionally, when a cyclic dienol ether of formula III, wherein $R^3$ is hydrogen and $R^4$ is $C_{1-4}$-alkoxy, is used, a compound represented by formula V is an intermediate product of this first process step:

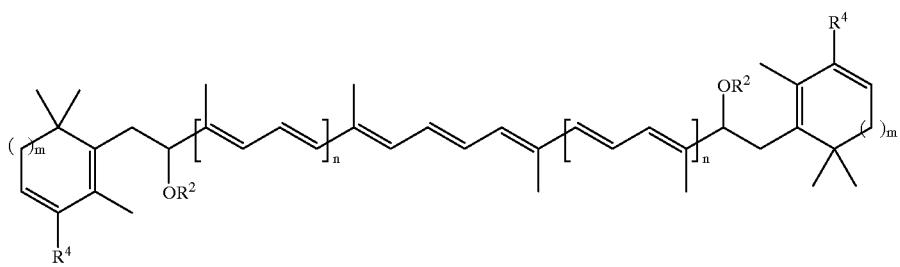

V wherein
  $R^2$ is $C_{1-6}$-alkyl;
  $R^4$ is $C_{1-4}$-alkoxy;
  m is 0 or 1; and
  n is 0, 1, or 2.

Alternatively, using a cyclic dienol ether of formula III wherein $R^3$ and $R^4$ together form the optionally substituted methylenedioxy group, the intermediate product of the first process step is a compound of the general formula

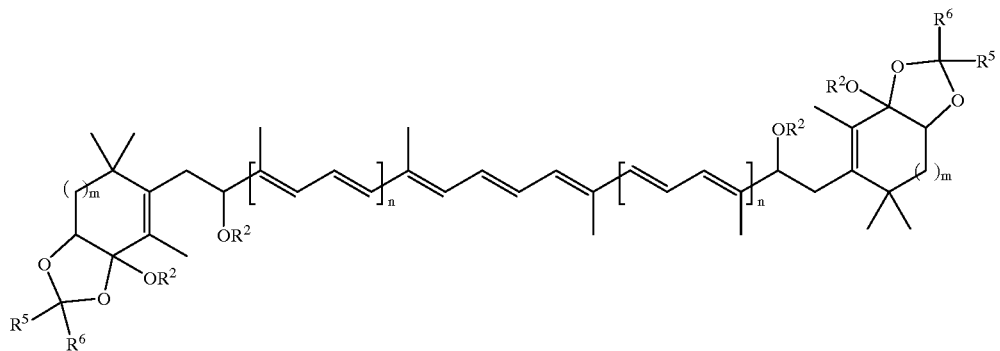

VI wherein $R^2$ is $C_{1-6}$-alkyl;

$R^5$ and $R^6$ are each independently hydrogen, $C_{1-4}$-alkyl, or phenyl;

m is 0 or 1; and n is 0, 1, or 2.

DETAILED DESCRIPTION OF THE INVENTION

As used throughout the scope of the present invention, the term alkyl as used in, e.g., "$C_{1-4}$-alkyl," "$C_{1-6}$-alkyl," and "$C_{1-4}$ alkoxy" embraces straight-chain and branched groups such as, methyl, ethyl, isobutyl, and hexyl. The term "lower" as used in, e.g., "lower aliphatic ether," embraces $C_{1-20}$, preferably $C_{1-10}$.

In the case of the cyclic dienol ethers of formula III there comes into consideration a substituted cyclopentene (m is 0, so that formula III then represents specifically the formula

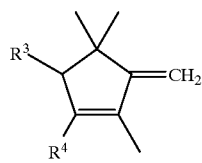

IIIa)

or a substituted cyclohexene (m is 1, so that formula III in this case specifically represents the formula

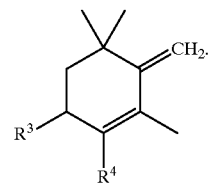

IIIb)

In this sense, there are to be understood under the corresponding terminal cyclic groups (rings), which the compounds of formulae I and IV have, groups of the formulae wherein * denotes the respective linkage position.

The formulae of polyenes and cyclic dienol ethers disclosed in the scope of the present invention embrace isomeric forms, e.g., optically active and cis/trans or E/Z isomers, as well as mixtures thereof unless expressly stated to the contrary. With respect to the E/Z isomerism, the (all-E) isomers of the polyene di(O,O-dialkyl acetals) of formula II and of the products of formula I of the process in accordance with the invention are, in general, preferred.

In the first process step of the process in accordance with the present invention, i.e., the reaction of the polyene di(O,O-dialkyl acetal) with the cyclic dienol ether under acidic conditions, an exclusive attack of the former compound at the γ-position of the cyclic dienol ether takes place. When a cyclic dienol ether of formula III, wherein $R^3$ is hydrogen and $R^4$ is $C_{1-4}$-alkoxy, is used, an intermediate product of this first process step is a compound of the general formula

V

Alternatively, using a cyclic dienol ether of formula III wherein $R^3$ and $R^4$ together form the optionally substituted methylenedioxy group, the intermediate product of the first process step is a compound of the general formula cooling the reaction mixture, for example to about $-10°$ C. to $-20°$ C., and filtration. Subsequently, the intermediate is then hydrolyzed with aqueous acid to the corresponding compound of formula IV.

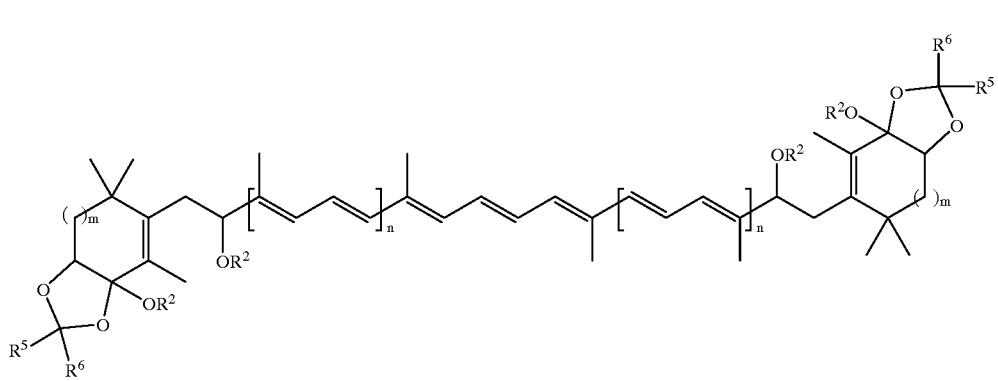

VI

This first process step is conveniently carried out by reacting the polyene di(O,O-dialkyl acetal) of formula II with the cyclic dienol ether of formula III in an organic solvent at temperatures in the range of about $-50°$ C. to about $+60°$ C. (e.g., from about $-25°$ C. to about $+60°$ C.), preferably in the temperature range of about $-30°$ C. to room temperature (e.g. from about $0°$ C. to room temperature), and in the presence of a Lewis or Brönsted acid. Suitable organic solvents are, in general, polar or non-polar aprotic solvents. Such solvents are, for example, lower halogenated aliphatic hydrocarbons, e.g., methylene chloride and chloroform; lower aliphatic and cyclic ethers, e.g., diethyl ether, tert.butyl methyl ether and tetrahydrofuran; lower aliphatic nitrites, e.g., acetonitrile; lower aliphatic esters, e.g., ethyl acetate; as well as, aromatic hydrocarbons, e.g., toluene. The preferred solvent is acetonitrile, optionally in combination with further aforementioned solvents, especially with ethyl acetate or methylene chloride. Where a mixture of acetonitrile with ethyl acetate or methylene chloride is used, the ratio by volume of acetonitrile to ethyl acetate or methylene chloride is preferably about 1:1 to about 4:1, particularly about 4:1. Examples of Lewis acids that can be used are zinc chloride, zinc chloride dietherate, zinc bromide, zinc di(trifluoromethanesulphonate), titanium tetrachloride, tin tetrachloride, boron trifluoride etherate as well as iron(III) chloride; and examples of Brönsted acids that can be used are p-toluenesulphonic acid, methanesulphonic acid, trifluoromethane-sulphonic acid, sulphuric acid, as well as, trifluoroacetic acid. In general, the Lewis acids, especially the zinc salts, boron trifluoride etherate, and iron(III) chloride, are preferred. The catalysts are, in general, used in catalytic (below stoichiomeric) amounts, conveniently in an amount which is about 0.5 to about 30 mol percent based on the amount of polyene di(O,O-dialkyl acetal) used, with the mol percent range preferably lying between about 5% and 10%. Further, there are conveniently used about 2.1 to about 4 equivalents, preferably about 2.2 to about 2.6 equivalents, of cyclic dienol ether per equivalent of polyene di(O,O-dialkyl acetal). Moreover, the reaction is conveniently effected at normal pressure with, in general, the pressure not being critical.

Frequently, the intermediates of formula V or of formula VI occur, usually together with diverse similar intermediates, as a precipitate, which can be isolated after When no isolation and subsequent hydrolysis is undertaken, a direct hydrolysis in the reaction mixture can be carried out. In so doing, an acid, preferably slightly dilute aqueous acetic acid, for example, with a ratio by volume acetic acid:water of about 9:1, is added to the reaction mixture and the mixture is subsequently stirred for a period, for example, about 30 minutes to about 2 hours, in the temperature range of about $0°$ C. to about $50°$ C. In addition to acetic acid, p-toluenesulphonic acid can also be used in a catalytic amount, such as about 1–2 mol percent based on the amount of polyene di(O,O-dialkyl acetal) used, in order to accelerate the hydrolysis. In comparison to the separate hydrolysis of the intermediate product of formula V or VI, the hydrolysis undertaken directly in the reaction mixture is preferred.

The product of formula of IV can be isolated from the reaction mixture and, if desired, purified in any manner per se. Typically, the mixture is combined with water and the whole is extracted with a water-immiscible organic solvent, such as, for example, a lower alkane, dialkyl ether, or aliphatic ester, e.g., hexane, tert.butyl methyl ether, or ethyl acetate, and the organic phase is washed with water and/or sodium bicarbonate solution and/or saturated aqueous sodium chloride solution, dried and concentrated. The thus-isolated and, at least to some extent, washed crude product can then, if desired, be purified further, for example, by column chromatography, e.g., using eluting agents, such as, hexane, ethyl acetate, toluene, or mixtures thereof, or recrystallization, for example from an alcohol, e.g., methanol or ethanol.

With respect to the last process step, i.e., the cleavage of the alkanol $R^2OH$ from the compound of formula IV, eliminations of the alkanol from β-alkoxyaldehydes or δ-alkoxy-α,β-unsaturated aldehydes with the formation of the corresponding α,β-unsaturated aldehydes are known in the specialist literature and can be carried out under a variety of conditions. For example, in the field of known base-induced eliminations, 1,8-diazabicyclo[5.4.0]undec-7-ene is very often used as the base in an amount of about 2 to 4 equivalents based on the amount of aldehyde used. Such conditions are used in the known production of carotenoids [see, inter alia, Bull. Chem. Soc. Japan 50, 1161 et seq. (1977), ibid. 51, 2077 et seq. (1978), Chem. Lett. 1975, 1201 et seq. and DOS 2,701,489] and of vitamin A (see, inter alia, Chem. Lett. 1975, 1201 et seq). As examples of acid-induced alkanol cleavages reference is again made to Bull. Chem. Soc. Japan 50, 1161 et seq. (1977) and to J. Gen. Chem. USSR 30, 3875 et seq. (1960) in which p-toluenesulphonic acid or 85% phosphoric acid is used as the acid catalyst. The buffer system sodium acetate/acetic acid [Helv. Chem. Acta. 39, 249 et seq. and 463 et seq. (1956) and U.S. Pat. Nos. 2,827,481 and 2,827,482] has been used for such a cleavage especially in the production of the carotenoids. Also, in the case of corresponding alkoxy ketones ($\beta$-alkoxyketones or $\delta$-alkoxy-$\alpha,\beta$-unsaturated ketones), the cleavage of the alkanol in general succeeds very well: see in this respect Synthesis 1986, 1004 et seq. or J. Org. Chem. 49, 3604 et seq. (1984). Taking into consideration this and other pertinent literature a person skilled in the art will have no difficulty in finding reaction conditions for the successful performance of the last step of the process in accordance with the invention.

Furthermore, the cleavage of the alkanol $R^2OH$ (2 equivalents per equivalent of the compound of formula IV) can also be carried out with several equivalent amounts of a base based on one equivalent of the compound of formula IV. Thus, the last process step in this case is conveniently carried out by converting the compound of formula IV, dissolved in a suitable organic solvent, into the corresponding polyene of formula I in the presence of a base with cleavage of the alkanol $R^2OH$. Suitable organic solvents are, in general, protic or aprotic solvents or mixtures thereof, such as, for example, alcohols, e.g., ethanol and isopropanol, and alcohol mixtures; or aromatic hydrocarbons, e.g., toluene. The base can be inorganic or organic, and, in general, there are suitable strong bases, especially those alkali metal alcoholates that are stronger bases, e.g., sodium ethylate. As indicated above, there are conveniently used at least two equivalents of base per equivalent of the compound of formula IV, preferably about 2.5 to about 8 equivalents.

When an alkali metal alcoholate is used as the base, either a solution of the sodium alkoxide in the alkanol is prepared in advance or this solution is prepared freshly from metallic sodium and the alkanol. The bringing together of the alkanolic solution of the sodium alkoxide with the solution or suspension of the compound of formula IV in the (same) alkanol, preferably likewise prepared in advance, can be effected in either sequence, as desired. The reaction mixture is then stirred while heating, suitable in the temperature range of about 60° C. to about 140° C., preferably at temperatures of about 80° C. to about 100° C. Depending on the boiling point of the solvent, the reaction is conveniently effected at normal pressure or with a slight excess pressure (in order to achieve the desired temperature), with, in general, the pressure not being critical. Under these conditions the cleavage reaction has normally finished after a few hours, especially after about 5 to 10 hours.

In the case of an acid-induced alkanol cleavage, suitable acids are, in general, strong mineral acids, such as, for example, hydrochloric acid, hydrobromic acid, hydroiodic acid, sulphuric acid, and perchloric acid, and sulphonic acids, such as, for example, methane-sulphonic acid, trifluoromethanesulphonic acid, and p-toluenesulphonic acid. The mineral acids can be aqueous and, depending on the acid, can have a concentration of about 10 to about 50%. Hydrochloric acid (especially about 10 to 37%), hydrobromic acid (especially about 25 to 30%) or hydroiodic acid (e.g., 47%) are the most suitable. In this case only a catalytic amount, i.e., up to a maximum of 1 equivalent per equivalent of the compound of formula IV, preferably about 0.1 to about 1 equivalent, is required. Further, the acid-induced alkanol cleavage is effected in a solvent in which the compound of formula IV has a good solubility (a so-called "homogeneous cleavage") or in a solvent in which this is not the case, i.e., in which the compound of formula IV is on the other hand in suspension ("heterogeneous cleavage"). In both cases, however, the acid catalyst need not be completely dissolved. Suitable solvents for the homogenous cleavage are especially halogenated aliphatic hydrocarbons, e.g., methylene chloride, chloroform and 1,2-dichloroethane, and aromatic hydrocarbons, e.g., benzene and toluene. Suitable solvents (dispersion media) for the heterogeneous cleavage are lower aliphatic nitrites, ketones, and carboxylic acids, e.g., acetonitrile, acetone, and acetic acid, preferably acetonitrile and acetone. In both cases, the alkanol cleavage is conveniently effected in the temperature range of about −20° C. to about +50° C., preferably in the range of about 0° C. to room temperature. The reaction time is, in each case, dependent on the reaction temperature and can be several hours, with the cleavage reaction normally having finished at the latest after about 5 hours.

Such an acid-induced alkanol cleavage is more suitable than a base-induced alkanol cleavage for the manufacture of astaxanthin, i.e., the compound of formula I, wherein $R^1$ is hydroxy and m and n are both 1.

As an alternative to the separate hydrolysis and alkanol cleavage, these two process steps can be carried out in a combined process step without isolation of the compound of formula IV using a somewhat stronger acid, especially a mineral acid, such as, for example, aqueous hydrochloric acid.

Irrespective of the chosen procedure for the last process step, the product can be isolated from the reaction mixture in any manner known per se, normally by cooling the reaction mixture, conveniently to room temperature or even to about 0° C., optional addition of water and filtration. After its isolation the product can be washed, for example with water and/or aqueous alcohol, and finally, if desired, dried under reduced pressure. If desired, further methods such as column chromatography and recrystallization can be used in order to arrive at a still purer product. Where an isomerization of the Z-isomers present in the product to the corresponding E-isomers is desired, a respective intermediate step can be included in the isolation and purification process. This intermediate step comprises adding an alcohol or aqueous alcohol, e.g., aqueous isopropanol, immediately after the cooling, heating the mixture in the temperature range of about 80° C. to about 100° C. and cooling the mixture and filtering off and drying the solid. Saturated lower hydrocarbons, e.g., heptane, also come into consideration as possible solvents. In general, the E-isomers are less soluble than the corresponding Z-isomers and accordingly often occur as a precipitate in higher yield. Furthermore, as mentioned above, the (all-E)-isomers of the products of formula I are, in general, preferred.

In the process in accordance with the invention defined above $R^2$ is preferably methyl, $R^3$ is preferably hydrogen and $R^4$ is preferably isobutoxy, or $R^3$ and $R^4$ together are preferably the methylenedioxy group ($R^5=R^6=$hydrogen), and n is preferably 1.

While some of the educts of the process in accordance with the invention are known, others can be produced according to methods known per se from precursors that are, to some extent, known.

For example, the novel polyene di(O,O-dialkyl acetals) of formula II can be prepared very simply in a known general manner by reacting the corresponding polyene dialdehyde of the formula

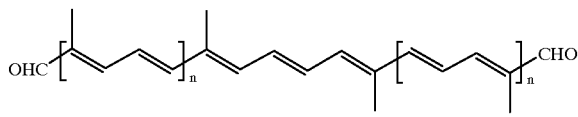

VII with the respective trialkyl orthoformate, especially in the corresponding $C_{1-6}$-alkanol, e.g., methanol for the O,O-dimethyl acetal, and in the presence of a catalytic amount of an organic acid or of a Lewis acid, e.g., p-toluenesulphonic acid, or zinc chloride [see, for example, Organikum, Organisch-chemisches Grundpraktikum, $6^{th}$ edition, p. 377 et seq. (1963)]. The reaction takes place to some extent in suspension, i.e., the respective polyene dialdehyde is suspended in the alkanol or in an alkanol/methylene chloride mixture and then there are added to the suspension about four mol equivalents of the trialkyl orthoformate, followed by a trace of acid catalyst, e.g., p-toluenesulphonic acid. In so doing, the dialdehyde dissolves slowly and the polyene di(O,O-dialkyl acetal) of formula II, which is formed simultaneously, crystallizes out slowly. The reaction is conveniently carried out in the temperature range of about 0° C. to about 40° C. and, as a rule, takes from 30 minutes to about 4 hours. As further background that illustrates the generally known acetalization method, reference is made to European Patent Publications 252 389 and 391 033, as well as, to J. Mol. Cat. 79, 117 et seq. (1993).

The polyene dialdehydes of formula VII, in turn, are either known, especially from the specialist literature concerning carotenoids, or, where novel, can be produced according to methods known per se. Thus, for example, the two-fold reaction of 2,7-dimethyl-2,4,6-octatriene-1,8-dial (the so-called "$C_{10}$-dial") with $C_5$- or $C_{10}$-Wittig aldehydes to give different chain-lengthened dialdehydes has become known from this literature. The text books "Carotinoids" (O. Isler, published by Birkhäuser Basel and Stuttgart, 1971, especially chapters VI and XII and the further literature mentioned therein) and "Carotinoids, Volume 2: Synthesis" (G. Britton, S. Liaaen-Jensen and H. Pfander, published by Birkhäuser Basel Boston Berlin, 1996, especially chapters III and VII), yield much useful information on the production and the occurrence of the known dialdehydes.

The cyclic dienol ethers of formula III are novel and represent a further aspect of the present invention.

Those cyclic dienol ethers of formula III, wherein $R^3$ is hydrogen, $R^4$ is $C_{1-4}$-alkoxy and m is 0, can be prepared in accordance with Reaction Scheme 1, starting from the known 2-methyl-1,3-cyclopentanedione, as follows:

Reaction Scheme 1

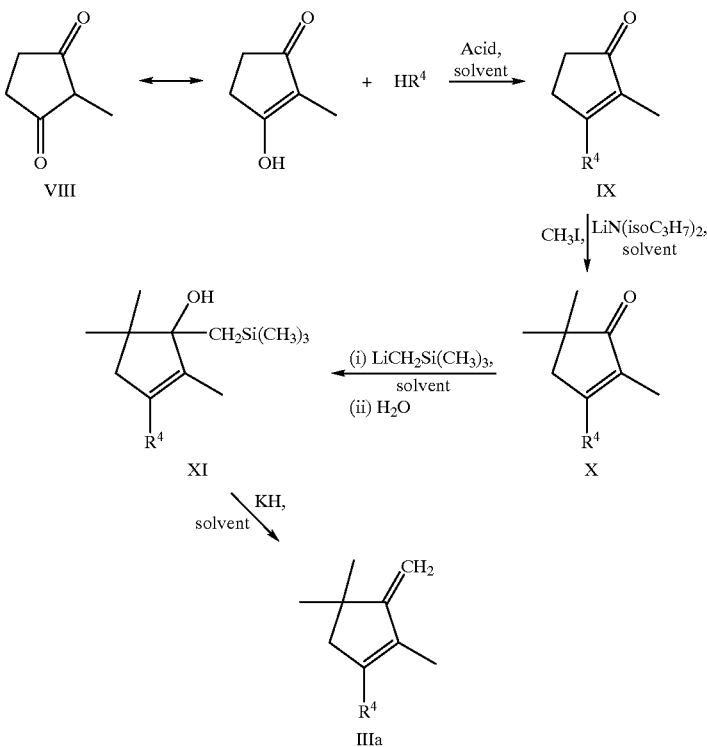

Those compounds of formula X wherein $R^4$ is methoxy or isobutoxy are known and can be produced according to the method of Rosenberger et al. [J. Org. Chem. 47, 2134 et seq. (1982)] from the commercially available 2-methyl-1,3-cyclopentanedione/1-hydroxy-2-methyl-cyclopenten-3-one of formula VIII by acid-catalyzed etherification with methanol or isobutanol to the corresponding compound of formula IX, followed by a double methylation with methyl iodide and lithium diisopropylamine at low temperature, e.g., at about −70° C. p-Toluenesulphonic acid/toluene is especially suitable as the acid catalyst/solvent combination for the first process step, VIII→IX, and tetrahydrofuran is preferably used as the solvent for the second process step. The remaining compounds of formula X wherein $R^4$ is $C_{1-4}$-alkoxy other than methoxy or isobutoxy can be produced in an analogous manner.

In accordance with the Peterson olefination [J. Org. Chem. 33, 780 et seq. (1968)], the keto enol ether of formula X is then reacted with trimethylsilylmethyllithium (itself produced from trimethylsilylmethyl chloride and metallic lithium in pentane) in pentane, and, after subsequent addition of water, gives the compound of formula XI in crystalline form. Subsequently, this can be converted directly with potassium hydride as the base and in tetrahydrofuran as the solvent at temperatures below room temperature, e.g., in the range of about 0° C. to about 15° C., into the desired cyclic dienol ether of formula IIIa. In so doing, the pentane used as the solvent in process step X→XI is replaced distillatively by the solvent of the last process step XI→IIIa (tetrahydrofuran) until a boiling point of about 62° C. (boiling point of tetrahydrofuran 66° C.) is attained. It is not necessary to isolate the compound of formula XI produced as the intermediate: by the solvent exchange and the thermal treatment this compound decomposes into the desired cyclic dienol ether of formula IIIa and the lithium salt of trimethylsilanol.

After the addition of water, the thus-obtained dienol ether is conveniently extracted with a suitable solvent, especially a lower alkane, e.g., pentane or hexane, or a lower aliphatic ether, e.g., diethyl ether, and thereafter purified by distillation under a high vacuum.

Those cyclic dienol ethers of formula III wherein $R^3$ is hydrogen, $R^4$ is $C_{1-4}$-alkoxy and m is 1 can be produced in accordance with Reaction Scheme 2 as follows:

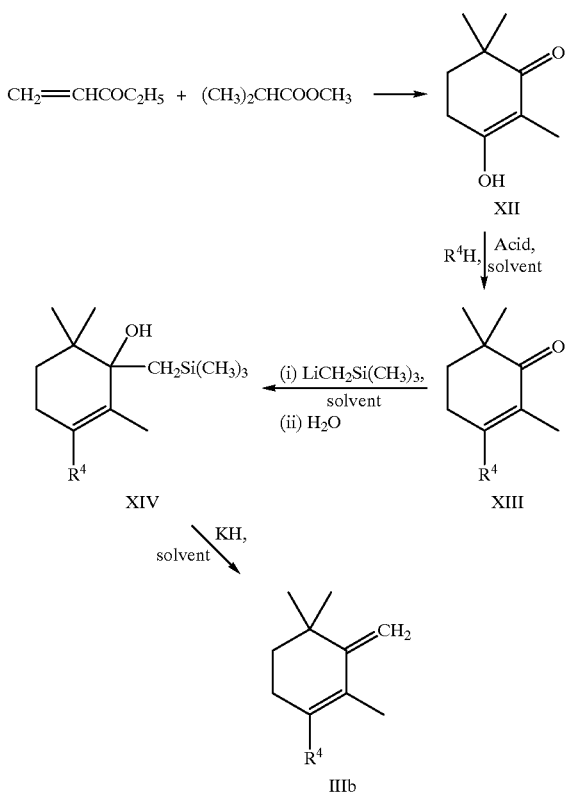

Those compounds of formula XIII wherein $R^4$ is methoxy, ethoxy, or isobutoxy are known [Tetr. Lett. 37) 1015 et seq. (1996) and, respectively, EP 31875] and can be produced according to the method of Rosenberger et al. [J. Org. Chem. p47, 2130 (1982)] from methyl isobutylate and ethyl vinyl ketone (by a Robinson annulation) followed by an acid-catalyzed etherification of the resulting 1-hydroxy-cyclohexen-3-one of formula XII with the corresponding alkanol to give the corresponding compound of formula XIII. Methanesulphonic acid or p-toluenesulphonic acid are especially suitable as the acid catalyst for the last process step XII→XIII and a lower alkane, e.g., hexane, or an aromatic hydrocarbon e.g., benzene or toluene, is especially suitable as the solvent. The remaining compounds of formula XIII wherein $R^4$ is $C_{1-4}$-alkoxy other than methoxy, ethoxy, or isobutoxy can be produced in an analogous manner.

The third and the last process step to the desired cyclic dienol ether of formula IIIb can be carried out analogously to process step X→XI and process step XI→IIIa for the production of the corresponding 5-ring compound [in accordance with the Peterson olefination, J. Org. Chem. 33, 780 et seq (1980)]. Although the compound of formula XIV can be isolated and purified by crystallization, it is, however, very unstable, especially in pure crystalline form; it readily rearranges in air into the compound of the formula

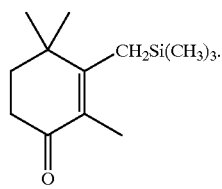

XV

Therefore, the compound of formula of XIV after crystallization and drying, conveniently under a high vacuum and while gassing with inert gas, e.g., argon, must be used as soon as possible in the next (last) process step. This last process step is conveniently effected in the presence of potassium hydride as the base and in tetrahydrofuran as the solvent at temperatures in the range of about 0° C. to about 15° C.

After the addition of water, the thus-obtained dienol ether is conveniently extracted with a suitable solvent, especially a lower alkane, e.g., pentane or hexane, or a lower aliphatic ether, e.g., diethyl ether, and purified thereafter by distillation under a high vacuum.

This production of the cyclic dienol ether of formula IIb is carried out more efficiently by reacting the compound of formula XIII with trimethylsilylmethyllithium in pentane at temperatures of about 0° C. to about −10° C. and, thereafter, replacing the pentane by tetrahydrofuran until the boiling point of tetrahydrofuran is achieved; this is thus a one-pot process. As in the above-described production of the cyclic enol ether of formula IIIa, the resulting intermediate of formula XIV decomposes into the desired cyclic enol ether of formula IIIb and the lithium salt of trimethylsilanol. Heating in tetrahydrofuran for too long a time should, however, be avoided, since under the prevailing basic conditions a partial isomerization of the resulting cyclic enol ether into the corresponding cyclohexadiene of the formula

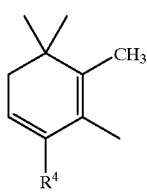

XVI can take place.

Finally, those cyclic dienol ethers of formula III wherein $R^3$ and $R^4$ together form an optionally substituted methylenedioxy group, —O—C($R^5$)($R^6$)—O—, can be produced in accordance with Reaction Scheme 3, starting from the known 1,5-dihydroxy-2,4,4-trimethyl-cyclopent-1-en-3-one or 1,6-dihydroxy-2,4,4-trimethyl-cyclohex-1-en-3-one, as follows:

The final products of the process in accordance with the invention, i.e., the symmetrical, terminal ring-substituted polyenes of general formula I, belong, for the most part, to the carotenoid field and can be used in a corresponding manner, for example as colorants or pigments for foodstuffs, egg yolk, the integuments (especially skin, legs and beak) and/or the subcutaneous fat of poultry, the flesh and/or the integuments (especially skin, scales and shell) of fish and crustaceans, etc. For example, astaxanthin is predominantly suitable as a pigment for the pigmentation of salmon. This use can be effected according to methods known per se as described, for example, in European Patent Publication No. 630,578.

The invention is illustrated on the basis of the following Examples:

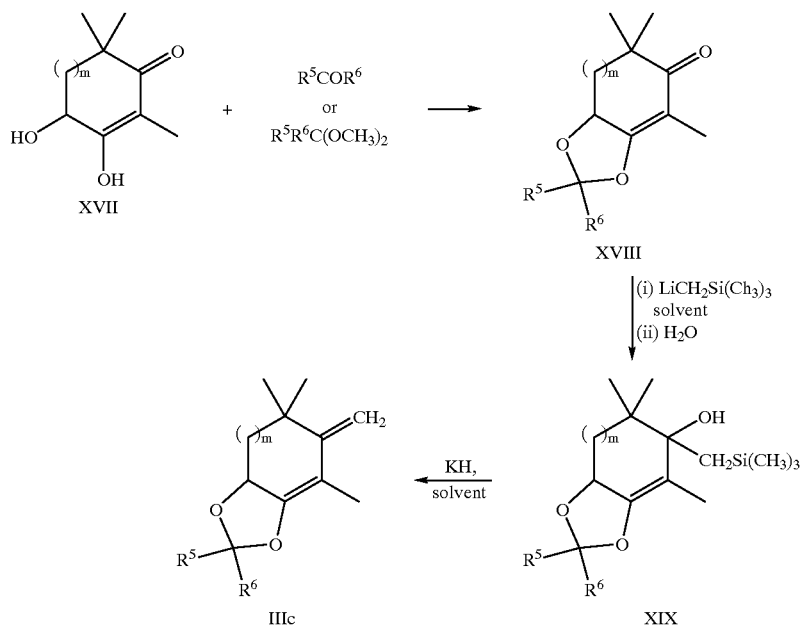

Reaction Scheme 3

The compound of formula XVII is acetalized in a manner known per se with a ketone $R^5COR^6$ or its dimethyl acetal to give the corresponding compound of formula XVIII [see Helv. Chim. Acta 64, 2436 et seq. (1981) and EP 0 085 158 A2]. Where acetone or its dimethyl acetal is used as the ketone or dimethyl acetal, the thus-obtained compound of formula XVIII wherein $R^5$ and $R^6$ are both methyl and m is 0 or 1 is known. However, formaldehyde or formaldehyde dimethyl acetal is preferably used as the acetalizing reagent, thereby producing the compound of formula XVIII, wherein $R^5$ and $R^6$ are both hydrogen, in high yield. The next two process steps XVIII→XIX and XIX→IIIc can be carried out analogously to process steps X→XI and XI→IIIa or XIII→XIV and XIV→IIIb of Reaction Schemes 1 or 2. The preferred product of this process is 4,6,6-trimethyl-5,6,7,7a-tetrahydro-5-methylidene-1,3-benzodioxol, i.e., the compound of formula IIIc wherein $R^5$ and $R^6$ are both hydrogen and m is 1.

Novel compounds within the scope of the present invention include the cyclic dienol ethers of formula III and the intermediates of formulae IV, V, and VI.

EXAMPLES

A. Preparation of polyene di(O,O-dialkyl acetals) (compounds of formula II)

Example 1

8,8'-Diapocarotenal dimethyl acetal (crocetin dialdehye dimethyl acetal)

15 g (50.1 mmol) of crocetin dialdehyde (≧99% pure according to HPLC) and 30 g (141 mmol) of trimethyl orthoformate were suspended in 50 ml of methylene chloride and 40 ml of methanol in a 500 ml round flask provided with a magnetic stirrer and argon gasification. 60 mg of p-toluenesulphonic acid monohydrate were added thereto at room temperature while stirring. The crystals present dissolved in about 2–3 minutes and a yellow precipitate formed after about a further 5 minutes. After stirring for about 40 minutes, 250 ml of methanol were added dropwise, followed by 0.3 ml of triethylamine. About 50 ml of solvent, i.e., methylene chloride, were subsequently distilled off under reduced pressure (350–400 mbar/35–40 kPa) at 30° C. during 30 minutes. Then, the remainder was cooled to 0° C. by means of an ice bath, filtered off, washed with methanol at −10° C. and dried at room temperature under a high vacuum. This gave 17.8 g of crocetin dialdehyde dimethyl acetal as yellow-orange crystals. Recrystallization from 50 ml of warmed methylene chloride and 260 ml of methanol added dropwise thereto while stirring and subsequent cooling to 0° C. gave, after filtration, washing with methanol at 10° C. and drying under a high vacuum at room temperature, 17.02 g (87% yield) of crocetin dialdehyde dimethyl acetal as yellow-orange crystals, m.p. 138° C., with a content of >99% according to HPLC; UV (hexane/2% methylene chloride): 456 nm (logE=4.63), 423 nm (logE=5.02), 398 nm (logE=4.90), 378 nm (logE=4.63); $^1$H-NMR ($C_6D_6$, 400 MHz): 1.83 (s, 6H), 1.87 (s, 6H), 3.18 (s, 12H), 4.59 (s, 2H), 6.25–6.70 (m, 10 olefinic H);

| Microanalysis: | | |
|---|---|---|
| Calc.: | C 74.19% | H 9.34% |
| Found: | C 74.10% | H 9.32% |

Example 2

8,8'-Diapocarotenal diethyl acetal (crocetin dialdehyde diethyl acetal)

10.0 g (33.4 mmol) of crocetin dialdehyde (≧99% pure according to HPLC) were suspended in 30 ml of methylene chloride and 70 ml of ethanol at room temperature in a 250 ml round flask provided with a magnetic stirrer and argon gasification. 22 g (140 mmol) of triethyl orthoformate and 50 mg of p-toluenesulphonic acid monohydrate were added thereto at room temperature while stirring. The crystals present dissolved in about 10–15 minutes and a dark green solution formed. After stirring at room temperature for a further 15 minutes, the mixture was neutralized with 0.5 ml of triethylamine and the methylene chloride was subsequently removed under reduced pressure (200–120 mbar/20–12 kPa). Thereby, orange crystals separated. A further 30 ml of ethanol were added, the mixture was cooled to 0° C. and the crystals were filtered off and washed with ethanol at −10° C. After drying under a high vacuum at room temperature, 11.23 g of crocetin dialdehyde diethyl acetal were obtained as a fine orange powder, m.p. 128–1290° C. Recrystallization from methylene chloride/ethanol at 0° C. gave 10.4 g (68% yield) of crocetin dialdehyde diethyl acetal as fine, yellow-orange crystals, m.p. 130–130.5° C., with a content of 97.5% according to HPLC; UV (cyclohexane/3% methylene chloride): 462 nm (logE=5.11), 434 nm (logE=5.10), 411 nm (logE=4.88); mass spectrum: 444 (M$^+$, 80); $^1$H-NMR ($C_6D_6$, 400 MHz): 1.26 (t, J=7 Hz, 6H), 1.94 and 2.04 (2s, in each case 3H), 3.50 and 3.70 (2 m, in each case 2H), 4.90 (s, 1H), 6.4–6.8 (5 olefinic H);

| Microanalysis: | | |
|---|---|---|
| Calc.: | C 75.63% | H 9.97% |
| Found: | C 75.44% | H 9.86% |

B. Preparation of the Cyclic Dienol Ethers (Compounds of Formula III)

Example 3

1-Isobutoxy-2,4,4-trimethyl-3-exomethylene-cyclopentene (formula III wherein $R^3$ signifies hydrogen $R^4$ signifies isobutoxy and m signifies 0)

(i) Preparation of 1-isobutoxy-2,4,4-trimethyl-cyclopenten-3-one

For the preparation of a solution of lithium diisopropylamine in tetrahydrofuran ("LDA solution"), 117 ml (830 mmol) of diisopropylamine were added dropwise to a mixture of 470 ml (750 mmol) of a 1.6M solution of butyllithium in hexane and 390 ml of tetrahydrofuran under argon within 30 minutes and the temperature was left to come slowly to −15° C.

430 ml (about 330 mmol) of the above LDA solution were placed at −70° C. in a 1.5l sulphonation flask provided with a mechanical stirrer, thermometer, 500 ml dropping funnel and argon gasification. 55 g (327 mmol) of 1-isobutoxy-2-methyl-cyclopenten-3-one were added dropwise thereto. The reaction mixture was then stirred at −70° C. for 20 minutes, subsequently treated slowly with 20.3 ml (46.3 g, 326 mmol) of methyl iodide and left to come to room temperature. After stirring at room temperature for 15 minutes the mixture was again cooled to −70° C. and a further 300 ml (230 mmol) of the above LDA solution were added dropwise, followed by 14.1 ml (32.1 g, 226 mol) of methyl iodide. The mixture was again left to come to room temperature and this procedure was repeated three times with 128 ml (98 mmol) of LDA solution and 6.1 ml (14 g, 100 mmol) of methyl iodide, 86 ml (66 mmol) of LDA solution and 4.0 ml (9 g, 65 mmol) of methyl iodide as well as 42 ml (32 mmol) of LDA solution and 2.0 ml (4.5 g, 32 ml) of methyl iodide. The reaction mixture was thereafter stirred at room temperature for one hour.

For the working up, there were added slowly thereto, initially dropwise, 100 ml of water and then 500 ml of diethyl ether, the aqueous phase was separated and the organic phase was washed with about 500 ml of saturated sodium chloride solution. The organic phase was then dried over anhydrous sodium sulphate and concentrated at 35° C. under reduced pressure. This gave 65 g of crude 1-isobutoxy-2,4,4-trimethyl-cyclopenten-3-one as a colorless oil.

This methylation reaction was repeated again in a wholly analogous manner starting from 49 g (291 mmol) of 1-isobutoxy-2-methyl-cyclopenten-3-one. A further 49 g of crude 1-isobutoxy-2,4,4-trimethyl-cyclopenten-3-one were obtained in this manner.

The crude products (together 114 g) of these two batches were purified by distillation over a short Vigreux column [b.p. about 83° C./0.4 mbar (40 Pa)]. This gave 85 g of product which partially solidified in the form of a glass. The product was dissolved in 500 ml of pentane and crystallized from the solution in a deep freezer (−25° C.). After filtration the crystals were dried at room temperature under a vacuum (14 mmHg), which gave 79.6 g (66% yield) of 1-isobutoxy-2,4,4-trimethyl-cyclopenten-3-one as snow-white platelets, m.p. 63° C. The content of the desired product according to gas chromatography (GC) was 100%.

(ii) Preparation of 1-isobutoxy-2,4,4-trimethyl-3-exomethylene-cyclopentene 170 ml of an about 0.8 M solution of trimethylsilylmethyllithium (about 140 mmol) in pentane [prepared by heating 3.3 g (0.48 mol) of lithium powder in 140 ml of pentane with 24.7 g (0.2 mol) of chloromethyltrimethylsilane at 40° C.

(reflux temperature) for about 16 hours, filtering under argon with a pressure suction filter and rinsing with about 20 ml of pentane; yield in each case about 80–85% according to titration: see J. Organomet. Chem 9, 165–168 (1967)] were placed in a 500 ml four-necked sulphonation flask provided with a mechanical stirrer, thermometer, dropping funnel and argon gasification. A solution of 23 g (112 mol) of 1-isobutoxy-2,4,4-trimethyl-cyclopenten-3-one (96% pure according to GC) in 50 ml of tetrahydrofuran was added dropwise thereto at −20° C. Then, the mixture was warmed to room temperature, a Vigreux column was fitted and solvent (pentane) was distilled off and continuous addition of tetrahydrofuran (finally 300 mol) was carried out until a head temperature of 62° C. was attained. Then, the mixture was cooled to 0° C. and treated dropwise with 150 ml of water. After extraction with pentane and washing the organic phase with saturated sodium carbonate solution and sodium chloride solution the organic phase was dried over anhydrous sodium sulphate, filtered and concentrated at 35° C. under reduced pressure. A distillation over a short Vigreux column [b.p. 49–55° C./0.40–0.45 mbar (40–45 Pa)] gave 17.24 g (78% yield) of 1-isobutoxy-2,4,4-trimethyl-3-exomethylene-cyclopentene as a colorless oil with a content of 99.4% according to GC. $^1$H-NMR (250 MHz, d6-DMSO) inter alia 4.37 (d, J~3 Hz, 2 olefinic H), 3.65 (d, J~7 Hz, 2H, —O—CH$_2$—CH); IR (film); 1659, 1619 cm$^{-1}$; mass spectrum: 194 (M$^+$, 65%).

| Microanalysis: | | |
|---|---|---|
| Calc.: | C 80.35% | H 11.41% |
| Found: | C 80.47% | H 11.32% |

Example 4

1-Isobutoxy-2,4,4-trimethyl-3-exomethylene-cyclohexene (formula III wherein R$^3$ signifies hydrogen, R$^4$ isobutoxy and m signifies 1; two stage process)

(i) Preparation of 1-isobutoxy-2,4,4-trimethyl-3-hydroxy-3-trimethylsilylmethyl-cylohexane 450 ml of a 0.8M solution of trimethylsilylmethyllithium (about 360 mmol/1.3 eq) in pentane [prepared from 7.1 g (1 mol) of lithium powder, 51 g (0.41 mol) of chloromethyl-trimethylsilane and 350 ml of pentane analogously to the method described in Example 3 (ii)/J. Organomet. Chem. 9, 165–168 (1967)] were placed in a 750 ml four-necked sulphonation flask provided with a magnetic stirrer, thermometer, dropping funnel and argon gasification. 60 g (0.278 mol) of 1-isobutoxy-2,4,4-trimethyl-cyclohexen-3-one (9.75% pure according to GC) were added dropwise to the solution at about −20° C. in about one hour, which gave rise to a slightly exothermic reaction. After completion of the addition the mixture was stirred at 0° C. in an ice bath for one hour until educt was no longer present according to GC.

100 ml of water were added slowly through the dropping funnel. Thereafter, the aqueous phase was separated and extracted twice with 50 ml each time, a total of 100 ml, of pentane. The combined organic phase was washed with 100 ml of saturated sodium chloride solution, dried with anhydrous sodium sulphate, and concentrated under reduced pressure. Crystallization from 125 ml of pentane while stirring at 50° C. for about one hour gave, after suction filtration and drying for about 18 hours under a high vacuum at room temperature, 75 g (90% yield) of 1-isobutoxy-2,4,4-trimethyl-3-hydroxy-3-trimethylsilylmethyl-cyclohexene as white crystals, m.p. about 50° C.; 1H-NMR (250 MHz, CDCl$_3$): inter alia 0.12 (s, 9H, Si(CH$_3$)$_3$), 1.80 (t, J=7 Hz, 2-CH$_2$), 1.86 (s, 2H, —CH$_2$—Si), 2.47 (t, J=7 Hz, 3-CH$_2$).

This product must be used immediately in the next step, as it is very unstable and readily rearranges into the oily compound of formula XV (see corresponding remarks in the general description).

(ii) Preparation of 1-isobutoxy-2,4,4-trimethyl-3-exomethylene-cyclohexene 60 ml of a potassium hydride suspension in oil (about 20%wt./vol., containing about 12 g/0.3 mol KH) were placed in a 750 ml four-necked sulphonation flask provided with a mechanical stirrer, thermometer, dropping funnel and argon gasification. The potassium hydride was washed three times with 25 ml each time, a total of 75 ml, of pentane, with the solvent being decanted off after each washing, and 200 ml of tetrahydrofuran were added thereto. After cooling the mixture to 5° C. by means of an ice bath a solution of the above 75 g (0.25 mol) of 1-isobutoxy-2,4,4-trimethyl-3-hydroxy-3-trimethylsilylmethyl-cyclohexene in 50 ml of tetrahydrofuran was added dropwise in about 1 hour at a maximum temperature of 10° C. The mixture was stirred at 15–20° C./1 hour and at room temperature/1 hour (GC control: about 96% product and no longer educt).

For the working up, the mixture was cooled to 0° C. and 200 ml of water were cautiously added dropwise. The two phases were now separated and the aqueous phase was extracted three times with 100 ml each time, a total of 300 ml, of pentane. The combined organic phases were washed with 100 ml of saturated sodium chloride solution, dried with anhydrous sodium sulphate and concentrated. The separated residue was again taken up in 250 ml of pentane, again dried with anhydrous sodium sulphate, filtered and concentrated under reduced pressure. This gave 58 g of crude 1-isobutoxy-2,4,4-trimethyl-3-exomethylene-cyclohexene as a yellowish liquid. A distillation at 0.1 mbar (10 Pa) over a small 10 cm Vigreux column gave at a boiling point of about 55–60° C. 51.2 g (93% yield) of 1-isobutoxy-2,4,4-trimethyl-3-exomethylene-cyclohexene as a colorless oil with a content of the desired product of 95% according to GC. $^1$H-NMR (C$_6$D$_6$, 250 MHz): 0.89 (d, J=7 Hz, 2×CH$_3$), 1.12 (s) 2×CH$_3$), 1.42 (t, J=7 Hz, 2-CH$_2$), 1.80 [heptet, J=7 Hz, —C$\underline{H}$—(CH$_3$)$_2$], 2.03 (t, J~2 Hz, 5-CH$_3$), 2.08 (bt, J~7 Hz, 3-CH$_2$), 3.28 (d, J=7 Hz, O—CH$_2$), 4.97 (d, J=10 Hz, =CH$_2$); IR (film): 1643, 1118 cm$^{-1}$.

| Microanalysis: | | |
|---|---|---|
| Calc.: | C 80.71% | H 11.61% |
| Found:. | C 80.64% | H 12.01% |

Example 5

1-Isobutoxy-2,4,4-trimethyl-3-exomethylene-cyclohexene (one stage process)

400 ml of a 0.76M solution of trimethylsilylmethyllithium (about 0.3 mol)/1.2 eq.) in pentane [prepared from 8.5 g (1.2 mol) of lithium powder, 50 g (0.4 mol) of chloromethyl-trimethylsilane and 300 ml of pentane analogously to the method described in Example 3 (ii)/J.Organomet. Chem 9, 165–168 (1967)] were placed in a 750 ml four-necked sulphonation flask provided with a mechanical stirrer, thermometer, 20 cm Vigreux column with distillation headpiece and argon gasification. 53 g (0.25 mol) of 1-isobutoxy-2,4,4-trimethyl-cyclohexen-3-one (97.5% pure according to GC) in 100 ml of tetrahydrofuran were added dropwise to the solution within 30 minutes at about −20° C., which gave rise to a slight exothermic reaction. The mixture was stirred at 0° C. for 1 hour, about 300 ml of pentane were subsequently distilled off through the Vigreux column and, after the addition of 200 ml of tetrahydrofuran, the distillation was continued until a boiling point of about 60° C. was attained (GC control: about 90% of desired product; educt and, respectively, intermediate no longer present).

Then, the mixture was cooled to +5° C., 200 ml of water were cautiously added dropwise and the mixture was worked up as in the previous experiment [Example 4 (ii)]. This gave 55 g of crude 1-isobutoxy-2,4,4-trimethyl-3-exomethylene-cyclohexene as a brownish oil which was distilled over a 10 cm Vigreux column under a high vacuum at 0.15 mbar (15 Pa). At a boiling point of 58–60° C. there were obtained 39 g (71% yield) of 1-isobutoxy-2,4,4-trimethyl-3-exomethylene-cyclohexene as a pale yellowish liquid. Content according to GC 94%; spectroscopic data as in Example 4 (ii).

Example 6

2,2,4,6,6-Pentamethyl-5,6,7,7a-tetrahydro-5-methylidene-1,3-benzodioxol (formula III wherein $R^3$ and $R^4$ together form isopropylidenedioxy and m is 1)

(i) Preparation of 2,2,4,6,6-pentamethyl-5,6,7,7a-tetrahydro-5-trimethylsilylmethyl-1,3-benzodioxol-5-ol About 500 ml of an about 0.8M solution of trimethylsilylmethyllithium (about 0.4 mol/2.0 eq.) in pentane [prepared from 5.2 g (0.75 mol) of lithium powder, 62.5 g (0.51 mol) of chloromethyltrimethylsilane and 250 ml of pentane analogously to the method described in Example 3 (ii)/J.Organomet. Chem. 9, 165–168 (1967)] were placed in a 1.5 l four-necked sulphonation flask provided with a mechanical stirrer, thermometer, dropping funnel and argon gasification. 42.0 g (0.2 mol) of 2,2,4,6,6-pentamethyl-5,6,7,7a-tetrahydro-1,3-benzodioxol-5-one in 140 ml of tetrahydrofuran were added dropwise to the solution within 30 minutes at about −20° C. Thereafter, the reaction mixture was left to warm slowly to 0° C. and then to warm to room temperature, at which temperature it was stirred for 30 minutes. After completion of the reaction, the mixture was again cooled to 0° C. and 200 ml of water were slowly added dropwise. The aqueous phase was separated and extracted twice with 100 ml, a total of 200 ml, of hexane. The organic phases were combined and washed with 100 ml of saturated sodium bicarbonate solution and 100 ml of saturated sodium chloride solution, dried over anhydrous sodium sulphate and concentrated at 40° C./30 mbar (3 kPa). This gave 59.6 of crude 2,2,4,6,6-pentamethyl-5,6,7,7a-tetrahydro-5-trimethylsilylmethyl-1,3-benzodioxol-5-ol as colourless, moist crystals. Recrystallization from 250 ml of pentane (after hot dissolution, cooling to about −20° C.) gave 49.3 g of pure product as white crystals, m.p. 95° C. A further 3.7 g of crystalline product, m.p. 95° C., could be obtained from the mother liquor, i.e., there were finally produced 53.0 g (89% yield) of 2,2,4,6,6-pentamethyl-5,6,7,7a-tetrahydro-5-trimethylsilylmethyl-1,3-benzodioxol-5-ol. $^1$H-NMR (CDCl$_3$, 250 MHz): inter alia. 0.06 (s, 9H, Si(CH$_3$)$_3$), 0.98 (s, 6H, C(6)-(CH$_3$)$_2$, 1.40 and 1.42 (2s, 6H, C(2)-(CH$_3$)$_2$), 4.43 (triplettoid, J~8 Hz, C$\underline{H}$—O); mass spectrum: 281 (M$^+$-OH, 5%), 242 (M$^+$-isobutylene, 100%).

| Microanalysis: | | |
|---|---|---|
| Calc.: | C 64.38% | H 10.13% |
| Found.: | C 64.10% | H 9.95% |

(ii) Preparation of 2,2,4,6,6-1pentamethyl-5,6,7,7a-tetrahydro-5-methylidene-1,3-benzodioxol 23 ml of a 20% suspension of potassium hydride in oil (containing about 3.7 g/92 mmol KH) were pipetted into a 500 ml round flask provided with a magnetic stirrer and dropping funnel having a fitted argon bubble counter and washed three times with 10 ml of hexane each time. Then, 120 ml of tetrahydrofuran were added thereto and a solution of 25.0 g (83 mmol) of 2,2,4,6,6-pentamethyl-5,6,7,7a-tetrahydro-5-trimethylsilylmethyl-1,3-benzodioxol-5-ol in 220 ml of tetrahydrofuran was added dropwise thereto at room temperature and the mixture was stirred at room temperature for 30 minutes (GC control: educt no longer present). Then, the mixture was cooled to 0° C. and 50 ml of water were slowly added dropwise. An analogous working up to that in (i) gave 29.7 g of crude 2,2,4,6,6-pentamethyl-5,6,7,7a-tetrahydro-5-methylidene-1,3-benzodioxol as a yellowish oil. A distillation on a very short Vigreux column gave at a boiling temperature of 50° C./0.02 mbar (2 Pa) 15.6 g (90% yield) of pure product as a colorless oil. $^1$H-NMR (CDCl$_3$, 250 MHz): inter alia 1.12 and 1.23 (2s, in each case 3H, C(6)-(CH$_3$)$_2$), 1.50 and 1.53 (2s, in each case 3H, C(2)(CH$_3$)$_2$), 1.73 (s, 3H, C(4)-CH$_3$), 4.55 (m, 1H, CH—O—), 4.79 (d, J=6 Hz, =CH$_2$); IR (film): 1693, 1112 cm$^{-1}$; mass spectrum: 208 (M$^+$, 40), 107(100);

| Microanalysis: | | |
|---|---|---|
| Calc.: | C 74.96% | H 9.68% |
| Found: | C 74.70% | H 9.42% |

Example 7

4,6,6-Trimethyl-5,6,7,7a-tetrahydro-5-methylidene-1,3-benzodioxol (formula III wherein $R^3$ and $R^4$ together form methylenedioxy and m is 1)

(i,a) Preparation of 4,6,6-trimethyl-5,6,7,7a-tetrahydro-1,3-benzodioxol-5-one (using formaldehyde dimethyl acetal)

85 g (0.5 mol) of 2,2,6-trimethyl-4,5-dihydroxy-cyclohex-5-en-1-one in 700 ml of ethyl acetate and 210 ml (2.4 mol) of formaldehyde dimethyl acetal were placed in a 2 l round flask and 5 g of Amberlyst® 15 (H$^+$ form) were added. Then, a soxhlet (500 ml; filled with molecular sieve 3 Å) with a condenser was fitted to the round flask. After reflux for a total of 10 hours the mixture was filtered off from the catalyst and concentrated at 35° C./62 mbar (6.2 kPa). After distillation over a 10 cm packed column, there were obtained at boiling point 78–84° C./0.3–0.15 mbar (30–15 Pa) 77.5 g (85% yield) of an oil, which solidified on cooling. 5 g of this product were recrystallized from 20 ml of pentane at up to −20° C. After filtration and drying under a high vacuum at room temperature this gave 4.50 g of 4,6,6-trimethyl-5,6,7,7a-tetrahydro-1,3-benzodioxol-5-one as white crystals, m.p. 55.5–57° C. IR (cm$^{-1}$): 1690, 1639; mass spectrum: 182 (M$^+$, 30), 126 (100); $^1$H-NMR (CDCl$_3$, 400 MHz): 1.16, 1.21 (2s, in each case 3H), 1.73 (s, 3H), 1.91 (t, J=19 Hz, 1H), 2.27 (q, J$_1$32 19 Hz, J$_2$=9 Hz, 1H), 4.6 (m, 1H), 5.32 (s, 1H), 5.61 (s, 1H).

| Microanalysis: | | |
|---|---|---|
| Calc.: | C 65.92% | H 7.74% |
| Found: | C 65.83% | H 7.79% |

(i,b) Preparation of 4,6,6-trimethyl-5,6,7,7a-tetrahydro-1,3-benzodioxol-5-one (using paraformaldehyde)

10.0 g (58 mmol) of 2,2,6-trimethyl-4,5-dihydroxy-cyclohex-5-en-1-one in 100 ml of ethyl acetate and 3.5 g (116 mmol) of paraformaldehyde were placed in a 250 ml round flask and 500 mg of Amberlyst® 15 (H$^+$ form) were added. The water formed was continuously distilled off azeotropically with ethyl acetate over a 30 cm Vigreux column (return ratio 10:1). After 2½ hours, 50 ml of ethyl acetate were added to the flask. After a further hour the reaction had finished according to thin layer chromatographic control. For the working up, the reaction solution was filtered and concentrated under reduced pressure. A short path distillation under a high vacuum at 0.3 mbar (30 Pa) and 100° C. bath temperature gave 9.8 g (93% yield) of oily distillate, which solidified on cooling. The product was identical with the product described under (i,a).

(ii) Preparation of 4,6,6-trimethyl-5,6,7,7a-tetrahydro-5-trimethylsilylmethyl-1,3-benzodioxol-5-ol 24.7 ml (20.6 g, 0.17 mol) of chloromethyltrimethylsilane were reacted with 2.92 g (0.42 mol) of lithium powder in 150 ml of pentane (according to the method described in Example 3). The resulting solution of trimethylsilylmethyllithium (about 0.14 mol) in pentane was placed in a 500 ml flask under argon gasification. A solution of 20 g (0.11 mol) of 4,6,6-trimethyl-5,6,7,7a-tetrahydro-1,3-benzodioxol-5-one in 25 ml of tetrahydrofuran was added thereto at −20° C. within about 20 minutes. After a further 20 minutes, the mixture was warmed slowly to room temperature and then cooled to 0° C. Thereafter, 90 ml of water were added dropwise thereto. Subsequently, the water was separated in a water separator and extracted twice with 100 ml of pentane each time. The pentane phases were washed in succession with sodium bicarbonate solution and sodium chloride solution, dried over anhydrous sodium sulphate and concentrated. The crude product (31.9 g) was then crystallized in 60 ml of pentane and cooled to −25° C. The resulting white crystals were filtered off, washed with a small amount of pentane at −20° C. and dried at room temperature under a high vacuum. This gave 30.5 g (almost 100% yield) of 4,6,6-trimethyl-5,6,7,7a-tetrahydro-5-trimethylsilylmethyl-1,3-benzodioxol-5-ol as white crystals, m.p. 63–64.5° C. IR (Nujol, cm$^{-1}$): 3510 (OH); mass spectrum: 253 (M$^+$-OH, 5), 214 (M-C$_4$H$_8$); $^1$H-NMR (C$_6$D$_6$, 400 MHz): inter alia 0.27 (s, 9H), 4.9 (s, 1H), 5.19 (s, 1H).

| Microanalysis: | | |
|---|---|---|
| Calc.: | C 62.18% | H 9.69% |
| Found: | C 62.07% | H 9.51% |

(iii) Preparation of 4,6,6-trimethyl-5,6,7,7a-tetrahydro-5-methylidene-1,3-benzodioxol 23 ml (about 1 eq.) of potassium hydride (20% in oil) were placed in a 750 four-necked sulphonation flask provided with a magnetic stirrer, dropping funnel and argon gasification, washed three times with hexane and 120 ml of tetrahydrofuran were added. A solution of 30.4 g (0.11 mol) of 4,6,6-trimethyl-5,6,7,7a-tetrahydro-5-trimethylsilylmethyl-1,3-benzodioxol-5-ol in 200 ml of tetrahydrofuran was added dropwise thereto at 0° C. Subsequently, the suspension was stirred at 20–30° C. for 2 hours. It was again cooled to 0° C. and 200 ml of water were cautiously added dropwise. Subsequent three-fold extraction with 100 ml of hexane each time, washing with saturated sodium chloride solution and drying over anhydrous sodium sulphate gave, after removal of the solvent under reduced pressure, 18.7 g of yellow oil which was subjected to short path distillation under reduced pressure. At 77–85° C./0.75 mbar (7.5 kPa) there were obtained 15.6 g (74% yield) of 4,6,6-trimethyl-5,6,7,7a-tetrahydro-5-methylidene-1,3-benzodioxol as a colorless oil. The content of desired product was 96% according to GC (area %). IR (film, cm$^{-1}$): 1697, 1600; mass spectrum: 180 (M$^+$, 50), 107 (100); 1H-NMR (C$_6$D$_6$, 400 MHz): inter alia 0.83 and 0.95 (2s, in each case 3H), 1.78 (bs, 3H), 3.9 (m, 1H), 4.59 (s, 1H), 4.70 (s, 1H), 4.75 (s, 1H), 4.91 (s 1H).

| Microanalysis: | | |
|---|---|---|
| Calc.: | C 73.30% | H 8.95% |
| Found: | C 73.08% | H 9.21% |

Example 8

4,6,6-Trimethyl-5,6,7,7a-tetrahydro-5-methylidene-1,3-benzodioxol ("through process")

The solution of trimethylsilylmethyllithium (about 0.43 mol) prepared from 8.7 g (1.25 mol) of lithium powder and 74 ml (61.6 g, 0.5 mol) of chloromethyltrimethylsilane in 450 ml of pentane was placed in a 750 ml four-necked sulphonation flask provided with a magnetic stirrer, dropping funnel, condenser and argon gasification. Then a solution of 60.0 g (0.33 mol) of 4,6,6-trimethyl-5,6,7,7a-tetrahydro-1,3-benzodioxol-5-one in 75 ml of tetrahydrofuran was added dropwise thereto at −20° C. within 30 minutes. The mixture was warmed slowly to room temperature and subsequently the pentane was distilled off up to the boiling point 62° C. over a Vigreux column. The pentane, which was distilled off, was replaced continuously with 500 ml of tetrahydrofuran. Finally, the mixture was heated at reflux for 12 hours under GC control. Subsequently, it was cooled to 0° C., 200 ml of water were added dropwise, the phases were separated and the aqueous phase was extracted three times with 100 ml of pentane each time. The entire organic phase was washed with 150 ml of saturated sodium bicarbonate solution and sodium chloride solution, dried over anhydrous sodium sulphate, filtered and concentrated. This gave 67.5 g of a yellow oil, which was distilled over a 10 cm packed column. At a boiling temperature of 38° C./0.04 mbar (4 Pa) there were obtained 49.0 g (82% yield) of 4,6,6-trimethyl-5,6,7,7a-tetrahydro-5-methylidene-1,3-benzodioxol as a colorless oil. The analytical data of the product were the same as those of the product of Example 7.

C. Preparation of the Symmetrical, Terminally Ring-substituted Polyenes (Compounds of Formula I)

Example 9

2,2'-Dinor-canthaxanthin (formula I wherein R$^1$ is hydrogen, m is 0 and n is 1; "through process" II+ III→[IV]→I)

3.4 g (8.6 mmol) of crocetin dialdehyde dimethyl acetal and 5.1 g (25 mmol) of 1-isobutoxy-2,4,4-trimethyl-3- exomethylene-cyclopentene (98% pure according to GC) in 60 ml of acetonitrile were placed in a 100 ml round flask provided with a magnetic stirrer, 400 mg (1.8 mmol, 20 mol %) of anhydrous zinc bromide were added and the reaction mixture was stirred at 50° C. for 16 hours. After this reaction period, an analysis by thin-layer chromatography with a 9:1 mixture of toluene and ethyl acetate as the eluent indicated that crocetin dialdehyde dimethyl acetyl ($R_f$=about 0.6) and the reaction product of formula IV ($R_f$=about 0.3) were present.

Then 30 ml of ethyl acetate were added to the dark solution obtained and the reaction mixture was cooled to 0° C. and, for the eventual hydrolysis, treated with 5 ml of a 9:1 mixture of acetic acid and water. The mixture was then stirred at this temperature for a further hour.

For the working up, the mixture was diluted with about 300 ml of ethyl acetate and the whole was washed in succession with in each case about 100 ml of water, saturated sodium bicarbonate solution and saturated sodium chloride solution. The organic phase was dried with anhydrous sodium sulphate and concentrated under reduced pressure at 35° C. This gave 6.8 g of crude 8,8'-dimethoxy-7,8,7',8', -tetrahydro-2,2'-dinor-canthaxanthin (respective compound of formula IV in which, inter alia, $R^2$ is methyl) as a viscous, red oil.

This oil was dissolved in 50 ml of ethanol and the solution was treated with 5.7 ml of a 1.6 molar solution of sodium ethylate in ethanol (containing 9 mmol of $NaOC_2H_5$). The reaction mixture was stirred at 80° C. for 2 hours and then cooled to 0° C. The separated dark crystals were filtered off under suction and dried at room temperature under a high vacuum, which gave 3.7 g of crude 2,2'-dinor-canthaxanthin as dark violet crystals. The crystals were taken up in 75 ml of isopropanol and the mixture was heated at reflux temperature for 16 hours. Recrystallization was subsequently carried out from methylene chloride/isopropanol (1:1), most of the methylene chloride being removed under reduced pressure. After filtration, washing and drying under a high vacuum at room temperature there were obtained 2.5 g (54% yield based on the diacetal of formula II) of 2,2'-dinor-canthaxanthin as dark violet crystals, m.p. 223–224° C.; UV (cyclohexane/2% methylene chloride): 527 nm (logE=5.02), 494 nm (logE=5.13), 468 nm (logE=5.02), 319 nm (logE=4.45); $^1$H-NMR (400 MHz, $CDCl_3$): inter alia 1.33 (s, 2×$CH_3$), 1.90, 2.00, 2.03 (3s, 3×$CH_3$), 2.35 (s, 3-$CH_2$); IR (KBr): 1685 $cm^{-1}$.

Mass spectrum: 536 ($M^+$, 100%).

Example 10

Preparation and isolation of the intermediate 8,8'-dimethoxy-7,8,7',8'-tetrahydro-2,2'-dinor-canthaxanthin (formula IV wherein $R^1$ is hydrogen, $R^2$ is methyl, m is 0 and n is 1)

A mixture of 1.18 g (3 mmol) of crocetin dialdehyde dimethyl acetal, 1.76 g (9 mmol) of 1-isobutoxy-2,4,4-trimethyl-3-exomethylene-cyclopentene and 135 mg (0.6 mmol, 20 mol %) of anhydrous zinc bromide in 25 ml of acetonitrile was stirred in a 50 ml round flask provided with a magnetic stirrer for 18 hours at 40° C. and subsequently for 6 hours at 50° C., during which the same control by thin-layer chromatography as described in Example 9 was carried out. Then the mixture was cooled to 0° C. and 2 ml of a 9:1 mixture of acetic acid and water, followed by 10 ml of ethyl acetate were added. After stirring the mixture at 0° C. for two hours a usual (as described in Example 9) working up, followed by a column chromatography on 150 g of silica gel (0.04–0.063 mm) with 9:1 toluene/ethyl acetate as well as a digestion from ethanol at 50° C. was carried out. This gave 230 mg (about 13% yield) of 8,8'-dimethoxy-7,8,7',8'-tetrahydro-2,2'-dinor-canthaxanthin as red crystals, m.p. 163–164° C. $^1$H-NMR ($CDCl_3$, 400 MHz): inter alia 1.18, 1.21 (2s, 12H, C(1)-$(CH_3)_2$, C(1')-$(CH_3)_2$), 2.29 (s, 4H, C(3)$H_2$, C(3')$H_2$, 2.45 (d×d, $J_1$=14 Hz, $J_2$=5 Hz, 2H, C(7)H, C(7')H), 2.69 (d×d, $J_1$=14 Hz, $J_2$=7 Hz, 2H, C(7)H, C(7')H), 3.13 (s, 6H, 2×$OCH_3$), 3.75 (d×d, $J_1$=7 Hz, $J_2$=5 Hz, C(8)H, C(8')H), 6.05–6.70 (m, about 10 olefinic H).

Mass spectrum: 600.5 ($M^+$, 25%).

Example 11

Canthaxanthin (formula I wherein $R^1$ is hydrogen and m and n are both 1)

(i) Preparation of 3,4,3',4'-tetradehydro-7,8,7',8'-tetrahydro-4,4'-diisobutoxy-8,8'-dimethoxy-β,β'-carotene (formula V wherein $R^2$ is methyl, $R^4$ is isobutoxy and m and n are both 1)

1.7 g (4.3 mmol) of crocetin aldehyde dimethyl acetal were suspended in 20 ml of acetonitrile and 5 ml of ethyl acetate in a 50 ml two-necked flask provided with a magnetic stirrer, thermometer and calcium chloride tube. 2.7 g (12.3 mmol) of 1-isobutoxy-2,4,4-trimethyl-3-exomethylene-cyclohexene and 120 mg (20 mol %) of anhydrous zinc chloride were added at 0–5° C. After a short time the ice bath was removed and the orange suspension was stirred at room temperature for about 20 hours. To the resulting lemon-yellow suspension was added 0.5 ml of triethylamine and the mixture was cooled to 0° C. and, after one hour, suction filtered. After drying under a high vacuum at room temperature, there were obtained 2.6 g (about 82% yield) of the compound named in the title as a pale yellow powder, m.p. 155–166° C.

For the analytical data, this product was refluxed twice, in each case for 30 minutes, in 25 ml of acetone, then cooled to −10° C. and filtered off under suction. After drying under a high vacuum at room temperature there were obtained 1.4 g of 3,4,3',4'-tetradehydro-7,8,7',8'-tetrahydro-4,4'-diisobutoxy-8,8'-dimethoxy-β,β'-carotene as a pale yellow powder, m.p. 166–173° C. UV (cyclohexane/2% chloroform): 430 nm (logE=5.16), 404 nm (logE=5.15), 383 nm (logE=4.93), 365 nm (logE=4.60; $^1$H-NMR ($C_6D_6$, 400 MHz): inter alia 0.89 (d, J=7 Hz, 12H, 2×CH$(CH_3)_2$), 1.20 (s, 6H, C(1)-$CH_3$, C(1')-$CH_3$), 1.23 (s, 6H, C(1')-$CH_3$, C(1')-$CH_3$), 3.09 (s, 6H, 2×$OCH_3$), 3.33 (d, J=7 Hz, 4H, 2×O—$CH_2$-), 4.59 (t, J~5 Hz, 2H, 2×C(3)H); IR (KBr): no C=O, 1650, 1089 $cm^{-1}$ (C—O—C); mass spectrum: 740.8 ($M^+$, ≦1%), 533.4 (15%), 326.1 (100%).

(ii) Preparation of 7,8,7',8-tetrahydro-8,8'-dimethoxy-canthaxanthin (formula IV wherein $R^1$ is hydrogen, $R^2$ is methyl and m and n are both 1)

1.00 g (1.35 mmol) of 3,4,3',4'-tetradehydro-7,8,7',8'-tetrahydro-4,4'-diisobutoxy-8,8'-dimethoxy-β,β'-carotene (m.p. 166–173° C.) was suspended in 10 ml of methanol in a 50 ml two-necked flask provided with a magnetic stirrer, thermometer and argon gasification and treated with 1 ml of 50% aqueous acetic acid, followed by 30 mg of p-toluenesulphonic acid monohydrate. The mixture was stirred at 35–40° C. for 3 hours. 2 ml of water were added thereto and the mixture was cooled to 0° C. and filtered. After drying under reduced pressure, there were obtained 800 mg (about 94% yield) of the compound named in the title as a yellow-orange powder, m.p. 183–189° C.

For the analytical data, 750 g of the product obtained were purified on silica gel (0.04–0.063 mm) with a 9:1 mixture of methylene chloride and diethyl ether. The pure fractions were concentrated and the residue was digested in 10 ml of methanol at reflux temperature for 2 hours. After cooling, filtration and drying under a high vacuum at room temperature there were obtained 370 mg of pure 7,8,7',8'-tetrahydro-8,8'-dimethoxy-canthaxanthin as a pale yellow powder, m.p. 200–203° C.; content according to HPLC: 96.5% (area %); UV (cyclohexane/3% chloroform): 429 nm (logE=5.14), 403 nm (logE=5.13), 382 nm (logE=4.90), 365 nm (logE=4.59); $^1$H-NMR (CDCl$_3$), 400 MHz): inter alia 1.14 (s, 6H, C(1)-CH$_3$, C(1')-CH$_3$), 1.19 (s, 6H, C(1)-CH$_3$, C(1')-CH$_3$), 2.40 (d×d, J$_1$=14 Hz, J$_2$=4 Hz, 2H, C(7)-H, C(7')-H), 2.65 (d×d, J$_1$=14 Hz, J$_2$=7 Hz, 2H C(7)H, C(7')H), 2.50 (t, J~7 Hz, 4H, C(3)H$_2$, C(3')H$_2$), 3.11 (s, 6H, 2×OCH$_3$), 3.70 (d×d, J$_1$=14 Hz, J$_2$=7 Hz, 2H, 2×CH—OCH$_3$), 6.0–6.7 (m, 10 olefinic H); IR (KBr): 1660 cm$^{-1}$(C=O); mass spectrum: 628.5 (M$^+$, 20), 477.3 (100).

| Microanalysis: | | | |
|---|---|---|---|
| Calc.: | C 79.62% | H 9.63% | (with 0.26% H$_2$O) |
| Found.: | C 79.43% | H 9.63% | (H$_2$O, 0.26%) |

Example 12

Canthaxanthin (formula I wherein R$^1$ is hydrogen and m and n are both 1 ("through process")

(i) Preparation of 3,4,3',4'-tetradehydro-7,8,7',8'-tetrahydro-4,4'-diisobutoxy-8,8'-dimethoxy-β,β'-carotene (formula V wherein R$^2$ is methyl, R$^4$ is isobutoxy and m and n are both 1)

60 mg (0.4 mmol, 5 mol %) of anhydrous iron(III) chloride and 5 drops of 1-isobutoxy-2,4,4-trimethyl-3-exomethylene-1-cyclohexene in a mixture of 25 ml of methylene chloride and 25 ml of ethyl acetate were placed in a 100 ml two-necked round flask provided with a magnetic stirrer, thermometer and argon gasification and the mixture was stirred at room temperature for 2 hours. Then, the mixture was cooled to −20° C. and 3.0 g (7.5 mmol) of crocetin dialdehyde dimethyl acetal (HPLC: ≧99% pure) and 4.0 g (19 mmol, 2.6 eq.) of 1-isobutoxy-2,4,4-trimethyl-3-exomethylene-1-cyclohexene were added in succession. The mixture was stirred at −20° C. to -15° C. for 2 hours and at −10° C. to −5° C. for a further 2 hours. A further 1.0 g (4.6 mmol) of 1-isobutoxy-2,4,4-trimethyl-3-exomethylene-1-cyclohexene was added and the mixture was stirred at −10° C. to −5° C. for a further 2 hours. Then the mixture was neutralized with 0.5 ml of triethylamine, 20 ml of methanol were added and the methylene chloride was removed under reduced pressure (350 mbar/35 kPa) at 20–30° C. The resulting orange crystals were now cooled at −5° C. for 2 hours. After suction filtration, washing (methanol, 0° C.) and drying under a high vacuum at room temperature for 18 hours there were obtained 5.3 g (about 95% yield) of 3,4,3',4'-tetradehydro-7,8,7',8'-tetrahydro-4,4'-diisobutoxy-8,8'-dimethoxy-β,β'-carotene as orange crystals, which were used immediately in the next reaction (ii).

(ii) Preparation of 7,8,7',8'-tetrahydro-8,8'-dimethoxy-canthaxanthin (formula IV wherein R$^1$ is hydrogen, R$^2$ is methyl and m and n are both 1)

5.2 g (about 7 mmol) of 3,4,3',4'-tetradehydro-7,8,7',8'-tetrahydro-4,4'-diisobutoxy-8,8'-dimethoxy-β,β'-carotene were suspended in 35 ml of methanol in a 100 ml two-necked round flask provided with a magnetic stirrer and argon gasification. 5 ml of 50% aqueous acetic acid and a small spatula tip of p-toluenesulphonic acid monohydrate were added to the suspension and the mixture was stirred at 40–45° C. for 3½ hours. After cooling the mixture to 3° C., 15 ml of water were added thereto and, after 30 minutes, the mixture was suction filtered using a P3 frit and washed with 10 ml of methanol at −20° C. After drying the product at room temperature under a high vacuum, there were obtained 4.0 g of the compound named in the title as orange crystals, m.p. 169–179° C. The crystals were recrystallized by dissolution in 30 ml of methylene chloride and replacement by 20 ml of methanol under reduced pressure [as described under (i)]. This gave 3.0 g (68% yield) of 7,8,7',8'-tetrahydro-8,8'-dimethoxy-canthaxanthin as orange crystals, m.p. 188–201° C. [isomer mixture; spectroscopic data: see Example 11 (ii)]. These were used immediately in the next reaction (iii).

(iii) Preparation of canthaxanthin 2.8 g (4.5 mmol) of 7,8,7',8'-tetrahydro-8,8'-dimethoxy-canthaxanthin were dissolved in 30 ml of methylene chloride in a 50 ml two-necked round flask provided with a magnetic stirrer, thermometer and argon gasification. Then the mixture was cooled to −15° C. and 1 ml (about 9 mmol) of 48% aqueous hydrobromic acid was added while stirring. After completion of the cleavage (after about 1¼ hours; HPLC control) 10 ml (about 10 mmol) of 1N sodium hydroxide solution were added in one portion and the mixture was stirred at 0° C. for 15 minutes. Then the aqueous phase was separated and extracted twice with 10 ml of methylene chloride each time. The combined organic phase was washed with 15 ml of saturated sodium bicarbonate solution, dried over anhydrous sodium sulphate and concentrated to about 20 ml. It was filtered over a 20 g pad of silica gel and back-washed with methylene chloride/diethyl ether (9:1). The filtered product was then concentrated under reduced pressure at about 100 mbar (10 kPa) and simultaneously exchanged against 20 ml of heptane.

The E/Z ratio prior to the isomerization was: (all E: 77%, (9Z+13Z): 13%.

For the isomerization, the mixture was boiled at reflux at about 100° C. for 7 hours, then cooled to room temperature and filtered. After drying at 70° C. under a high vacuum for 4 hours there were obtained 2.3 g (about 82% yield) of crude canthaxanthin as brown-violet crystals with a HPLC content (area %) of 90.5% (all E). For recrystallization, the crude product was dissolved in 30 ml of methylene chloride and exchanged against 15 ml of acetone at about 100 mbar (10 kPa). After cooling at −25 ° C. for 2 hours the crystals were filtered off, washed with acetone at 0° C. and dried at 70° C. under a high vacuum for 4 hours. This gave 2.0 g (76% yield) of canthaxanthin as deep violet crystals, m.p. 207–208° C.; HPLC content (area %):

(all E)-canthaxanthin: 95.7%
(9Z+13Z)-canthaxanthin: 1.6%
8'-apocanthaxanthinal: 2.1%

UV (cyclohexane/3% CHCl$_3$): 470 nm (logE=5.09); IR (KBr): 1657 cm$^{-1}$; mass spectrum: 564 (M$^+$, 22); $^1$H-NMR (400 MHz, CDCl$_3$): 1.20 (s, 12H), 1.85 (t, J~8 Hz, 4H), 1.87 (s, 6H), 1.99 and 2.00 (2s, 12H), 2.50 (t, J~7 Hz, 4H), 6.2–6.7 (div. m, 14H).

Example 13

Preparation and isolation of the intermediate 8,8'-dimethoxy-7,8,7',8'-tetrahydro-3,3'-dihydroxy-4,4'-diketo-β,β'-carotene (formula IV wherein R$^1$ is hydroxy, R$^2$ is methyl and m and n are both 1)

582 mg (1.5 mmol) of crocetin dialdehyde dimethyl acetal (HPLC: >97% pure) and 937 mg (4.5 mmol) of 2,2,4,6,6- pentamethyl-5,6,7,7a-tetrahydro-5-methylidene-1,3-benzodioxol were placed in 8 ml of acetonitrile in a 25 ml round flask provided with a magnetic stirrer and argon gasification. After the addition of 25 mg (0.2 mmol) of anhydrous zinc chloride the reaction solution was stirred at room temperature for 16 hours under control by thin layer chromatography. The resulting dark red solution was then concentrated and the oil obtained was purified on 50 g of silica gel (0.04–0.063 mm) with methylene chloride/diethyl ether (9:1) as the solvent. This yielded 331 mg (33% yield) of orange crystals. For further purification for the spectroscopic date, they were digested in hot methanol, cooled to −20° C., filtered off and dried under a high vacuum. This gave 190 mg of 8,8'-dimethoxy-7,8,7',8'-tetrahydro-3,3'-dihydroxy-4,4'-diketo-β,β'-carotene as pale orange crystals, m.p. 171° C.; HPLC: 99.5% pure; UV (cyclohexane/3% CHCl$_3$): 429 nm (logE=5.12), 403 nm (logE=5.11), 382 nm (logE=4.90); IR (KBr): 1657 cm$^{-1}$; $^1$H-NMR (CDCl$_3$, 400 MHz): inter alia 1.17, 1.23, 1.24, 1.28 (4s, 12H), 3.09, 3.10 (2s, 2×OCH$_3$), about 3.7 (m, 4H), 4.3 (m, 2H), 61–6.7 (10 olefinic H).

|  | Microanalysis: |  |
|---|---|---|
| Calc.: | C 76.33% | H 9.15% |
| Found: | C 76.13% | H 9.18% |

Example 14

Preparation of 3,3'-dihydroxy-4,4'-diketo-β,β'-carotene, i.e., of astaxanthin (formula I wherein R$^1$ is hydroxy and m and n are both 1; "through process" II+III→I)

580 mg (1.5 mmol) of crocetin dialdehyde dimethyl acetal (HPLC: >97% pure) and 940 mg (4.5 mmol) of 2,2,4,6,6-pentamethyl-5,6,7,7a-tetrahydro-5-methylidene-1,3-benzodioxol were placed in 8 ml of acetonitrile in a 25 ml round flask provided with a magnetic stirrer and argon gasification. After the addition of 50 mg (0.4 mmol) of anhydrous zinc chloride, the reaction solution was stirred at room temperature for 2½ hours under control by thin layer chromatography. The dark coloured suspension was cooled to −20° C. and 5 drops of 37% aqueous hydrochloric acid were added. After 5 minutes the mixture was warmed to 0° C. and stirred at this temperature for a further 15 minutes. Subsequently, the reaction solution was poured into 100 ml of water and extracted twice with 50 ml of methylene chloride each time. The thus-obtained dark red, oily crude product was chromatographed on 70 g of silica gel (0.04–0.063 mm) with methylene chloride/diethyl ether (5:1). In this manner there were obtained 358 mg (40% yield) of astaxanthin as dark red crystals (uniform according to thin layer chromatography). For the spectroscopic data, 320 mg were digested in hot methanol, cooled, filtered off and dried under a high vacuum. This gave 198 mg of astaxanthin as glistening, deep violet crystals, m.p. 212–218° C. IR (KBr): 1657, 1610 cm$^{-1}$; mass spectrum: 596.5 (M$^+$, 40); $^1$H-NMR (CDCl$_3$,400 MHz): 1.29, 1.32 (2s, 2×6H), 1.84 (t, J=12 Hz, 2H), 1.94 (s, 2×3H), 2.00, 2.03 (2s, 2×6H), 2.16 (q, J=6 Hz, 2H), 3.68 (d, J~1–2 Hz, 2H), 4.8 (m, 2H), 6.2–6.7 (14 olefinic H).

Example 15

Preparation of 8,8'-diethoxy-7,8,7',8'-tetrahydro-3,3'-dihydroxy-4,4'-diketo-β,β'-(3'-carotene (formula IV wherein R$^1$ is hydroxy, R$^2$ is ethyl and m and n are both 1)

20 ml of methylene chloride were placed in a 50 ml round flask provided with a mechanical stirrer and argon gasification and about 40 mg (4 drops; 0.4 mmol) of acetone dimethyl acetal and about 25 mg (2 drops; 0.2 mmol, 8 mol %) of boron trifluoride diethyl etherate were added. After stirring this solution at room temperature for one hour (to remove the residual water from the solvent), it was cooled to −25° C., 1.11 g (2.5 mmol) of crocetin dialdehyde diethyl acetal and 1.30 g (7.2 mmol) of 4,6,6-trimethyl-5,6,7,7a-tetrahydro-5-methylidene-1,3-benzodioxol were added thereto in succession without solvent and the mixture was stirred at −20 to −25° C. under control by HPLC.

For the hydrolysis, 4 ml of 90% aqueous acetic acid were added at −20° C. and the mixture was stirred at room temperature for 10 minutes. Then, it was poured into water and extracted twice with 100 ml of hexane each time, washed with saturated sodium bicarbonate solution and saturated sodium chloride solution, dried with anhydrous sodium sulphate, filtered and concentrated. This gave 2.80 g of red oil which was chromatographed on 100 g of silica gel (0.04–0.63 mm) with methylene chloride/diethyl ether (9:1). There was isolated 1.00 g (58% yield) of 8,8'-diethoxy-7,8,7',8'-tetrahydro-3,3'-dihydroxy-4,4'-diketo-β,β'-carotene as a reddish solid; HPLC content: 98.1% (area %). For the spectroscopic data, this substance was digested in 15 ml of hot methanol, cooled to −20° C., filtered off and dried under a high vacuum. There were thus obtained 620 mg of orange crystals, m.p. 140–150° C., with a content of 98.8% (area %) according to HPLC. UV (cyclohexane/3% CHCl$_3$): 429 nm (logE=5.14), 403 nm (logE=5.13), 382 nm (logE=4.91); IR (Nujol): 1664 cm$^{-1}$, 1607 cm$^{-1}$; mass spectrum: 688.6 (M$^+$, 5), 521.4 (30); $^1$H-NMR (CDCl$_3$, 400 MHz; diastereomer mixture): inter alia 2.3 (dxd, J$_1$=14 Hz, J$_2$=3 Hz, 1H), 2.45 (dxd, J$_1$=14 Hz, J$_2$=4.5 Hz, 1H), 2.6 (dxd, J$_1$=14 Hz, J$_2$=7.5 Hz, 1H), 2.7 (dxd, J$_1$=14 Hz, J$_2$=8,5 Hz, 1H), 3.1 and 3.35 (2m, 4H, 2×OCH$_2$), 3.65 (2d, J~6 Hz, 2×OH), 3.8 (m, 2H, CH-OC$_2$H$_5$), 4.3 (m, 2H, CH-OH), 6.1–6.7 (div. m, 10 olefinic H).

| Microanalysis (20 mol % methanol in the crystals): | | |
|---|---|---|
| Calc.: | C 76.34% | H 9.36% |
| Found: | C 75.92% | H 9.02% |

Example 16

Preparation of 3,3'-dihydroxy-4,4'-diketo-β,β'-carotene, i.e., of astaxanthin (formula I wherein R$^1$ is hydroxy and m and n are both 1; "through process")

60 ml of methylene chloride were placed in a 100 ml four-necked sulphonation flask provided with a mechanical stirrer, thermometer and argon gasification and about 55 mg (6 drops, 0.5 mmol) of acetone dimethyl acetal and about 25 mg (2 drops, 0.2 mmol, 2 mol %) of boron trifluoride diethyl etherate were added. After leaving this solution to stand at room temperature for about 16 hours (to remove residual water), it was cooled to −25° C. and 3.33 g (7.3 mmol) of crocetin dialdehyde diethyl acetal (HPLC: 97.5% pure) and 380 g (21 mmol, 29 eq.) of 4,6,6-trimethyl-5,6,7,7a-tetrahydro-5-methylidene-1,3-benzodioxol were added thereto in one portion and without solvent. Then the mixture was stirred at −20° C. to −15° C. for 9 hours under HPLC control. 0.7 ml (about 1 g, 6 mmol) of 48% aqueous hydrobromic acid were added thereto at −20° C. and the mixture was stirred at this temperature for 30 minutes.

For the neutralization, 10 ml (10 mmol) of 1N sodium hydroxide solution were added to the mixture in one portion. Subsequently, the mixture was stirred in an ice bath at 0° C. for 45 minutes and then acidified with 1 ml of acetic acid. Then, the reaction solution was extracted with methylene chloride, washed twice with water, dried over anhydrous sodium sulphate and concentrated. This gave 5.84 g of a dark red, solid residue, which was suspended in 60 ml of heptane. The suspension was refluxed at 100° C. for 3 hours, cooled slowly to room temperature and filtered. The crystals obtained were washed with heptane. After drying the crystals at room temperature under a high vacuum there were obtained 4.10 g of a brown-red powder. This was recrystallized by dissolution in methylene chloride (60 ml or 35 ml) and continuous replacement by acetone (40 ml or 30 ml) under reduced pressure. Cooling (−20° C.) and washing with cold (−20° C.) acetone gave, after drying at 55° C. for one hour under a high vacuum, 2.20 g (45% yield based on crocetin dialdehyde diethyl acetal used) of astaxanthin as violet, glistening crystals, m.p. 219° C.; HPLC: 97% (area %).

For the analytical data, recrystallization was carried out two more times. This gave astaxanthin as metallically glistening crystals, m.p. 219° C.; HPLC: 97% (area %); HPLC (wt. % compared with standard):

(all E)-astaxanthin: 94%
(9Z+13Z)-astaxanthin: 0.3%
mono-ethoxymethoxy-astaxanthin: 1.6%
8'-apoastaxanthinal: 1.6%
3,3'-dihydroxy-2,3-didehydro-4,4'-diketo-β,β'-carotene ("halbastacin"): 0.1% methylene chloride: 2%
UV (cyclohexane/3% $CHCl_3$): 476 nm (log E=5.10).

| Microanalysis (corrected with 2% methylene chloride in the crystals): | | |
|---|---|---|
| Calc.: | C 78.95% | H 8.65% |
| Found: | C 78.79% | H 8.52% |

Example 17

Preparation and isolation of the intermediate 4,8,4',8'-tetramethoxy-7,8,7',8'-tetrahydro-3,4,3',4'-bis(O-methylene)-β,β'-carotene (formula VI wherein $R^2$ is methyl, $R^5$ and $R^6$ are both hydrogen and m and n are both 1)

(a) Catalysis by Zinc Chloride, with Acetonitrile as the Solvent 580 mg (1.5 mmol) of crocetin dialdehyde dimethyl acetal (HPLC: >97% pure) and 815 mg (4.5 mmol) of 4,6,6-trimethyl-5,6,7,7a-tetrahydro-5-methylidene-1,3-benzodioxol were placed in 10 ml of acetone in a 25 ml round flask provided with a magnetic stirrer and argon gasification and the mixture was treated with about 20 mg (10 mol %) of anhydrous zinc chloride at 0° C. The resulting orange suspension was then stirred at −5° C. for 4 days and thereafter at room temperature for 5 days, with a pale yellow suspension resulting. It was cooled to −10° C., suction filtered and washed with 8 ml of acetonitrile at −20° C. For purification, the yellow crystals were digested in 10 ml of hot methanol, cooled to −10° C., filtered off and dried at room temperature under a high vacuum. This gave 690 mg (62% yield) of 4,8,4',8'-tetramethoxy-7,8,7'8'-tetrahydro-3,4,3',4'-bis(O-methylene)-β,β'-carotene as an orange powder.

For the analytical data, a sample was again digested from acetone in an analogous manner. This gave pale orange crystals, m.p. 170.5° C. UV (cyclohexane/3% $CHCl_3$): 429 nm (logE=5.14), 403 nm (logE=5.12), 382 nm (logE=4.91); IR ($cm^{-1}$): no C=O bands; mass spectrum: 748.5 ($M^+$, 5), 537.3 (50), 179 (100); $^1H$-NMR (d6-DMSO, 400 MHz; diastereomer mixture): inter alia 3.05, 3.17 (2s, $OCH_3$), 3.70 (2m, C(3)-H), 4.98 and 5.07 (2m, $OCH_2O$), 6.10–6.70 (div. m, olefinic H).

| Microanalysis (with 0.4% $H_2O$): | | |
|---|---|---|
| Calc.: | C 74.16% | H 8.66% |
| Found: | C 74.07% | H 8.96% |

(b) Catalysis by Zinc Di(Trifluorosulphonate), with Acetonitrile as the Solvent 72 mg (about 8 drops) of acetone dimethyl acetal followed by 43 mg (0.12 mmol, 1.2 mol %) of zinc triflate were added to 40 ml of acetonitrile and the mixture was stirred for about 16 hours. Then 4.01 g (10 mmol) of crocetin dialdehyde dimethyl acetal (HPLC: ≧97% pure) and 4.60 g (25.6 mmol, 2.6 eq.) of 4,6,6-trimethyl-5,6,7,7a-tetrahydro-5-methylidene-1,3-benzodioxol were added thereto at 0° C. and the mixture was stirred at 0° C. for 8 hours and at room temperature for 24 hours. In an analogous manner to that described under (a), after neutralization with about 0.2ml of triethylamine the mixture was cooled to −20° C. and the thick yellow paste was filtered off and dried at room temperature under a high vacuum. This gave 7.06 g (94% yield) of 4,8,4',8'-tetramethoxy-7,8,7',8'-tetrahydro-3,4,3',4'-bis(O-methylene)-β,β'-carotene as orange crystals.

(c) Catalysis by Iron(III) Chloride, with Methylene Chloride as the Solvent 100 mg (1 mmol) of acetone dimethyl acetal and 76 mg (0.5 mmol, 4 mol %) of anhydrous iron (III) chloride in 100 ml of methylene chloride were left to stand for about 16 hours in a 150 ml round flask provided with a magnetic stirrer and argon gasification. Then the mixture was cooled to −30° C. and 5.6 g (14.0 mmol) of crocetin dialdehyde dimethyl acetal (HPLC: >97% pure) followed by 6.5 g (36 mmol) of 4,6,6-trimethyl-5,6,7,7a-tetrahydro-5-methylidene-1,3-benzodioxol were added thereto in one portion without solvent. The mixture was stirred at −25 to 30° C. for 7 hours under control by HPLC. 0.5 ml of triethylamine was added for the neutralization of the catalyst, the methylene chloride was replaced slowly by about 90 ml of methanol under reduced pressure (150 mbar=15 kPa), the mixture was cooled to −20° C. and the resulting crystals were filtered off, washed with cold (−20° C.) methanol and dried under a high vacuum for about 16 hours. This gave 9.90 g (94% yield) of 4,8,4',8'-tetramethoxy-7,8,7',8'-tetrahydro-3,4,3',4'-bis(O-methylene)-β,β'-carotene as yellow-orange crystals, m.p. 169–172° C. Mass spectrum: 748.5 ($M^+$, 2), 537.3 (10); $^1H$-NMR ($C_6D_6$, 400 MHz; diastereomer mixture): inter alia 2.40, 2.75 (2m, 4H), 3.12 (s, $OCH_3$, 6H), 3.35 (2s, $OCH_3$, 6H), 3.8 (m, 2H), 4.6 (m, 2H), 5.11 and 5.14 (2s, 2H), 5.33 (s, 2H), 6.3–6.8 (m, 10 olefinic H).

(d) Catalysis by Boron Trifluoride Diethyl Etherate, with a Mixture of Methylene Chloride and Acetonitrile as the Solvent An analogous reaction [as described under (b)] of 2.72 g (6.8 mmol) of 2.72 g (6.8 mmol) of crocetin dialdehyde dimethyl acetal (HPLC: ≧97% pure) with 3.28 g (18.2 mmol) of 4,6,6-trimethyl-5,6,7,7a-tetrahydro-5-methylidene-1,3-benzodioxol in a mixture of 50 ml of methylene chloride and 10 ml of acetonitrile with about 40 mg (3 drops, 0.3 mmol, 4 mol %) of boron trifluoride diethyl etherate at −30° C. over 2 hours gave, after neutralization with triethylamine and crystallization [analogously to (c)], 4.71 g (92% yield) of 4,8,4',8'-tetramethoxy-7,8,7',8'-tetrahydro-3,4,3',4'-bis(O-methylene)-β,β'-carotene as straw-yellow crystals, m.p. 175–177° C.

Example 18

Preparation of 3,3'-dihydroxy-4,4'-diketo-β,β'-carotene, i.e., of astaxanthin (formula I wherein $R^1$ is hydroxy and m and n are both 1)

(a) Hydrolysis and Cleavage in Methylene Chloride 4.90 g (6.55 mmol) of 4,8,4',8'-tetramethoxy-7,8,7',8'-tetrahydro-3,4,3',4'-bis(O-methylene)-β,β'-carotene were dissolved in 60 mnl of methylene chloride in a 100 ml round flask provided with a magnetic stirrer and argon gasification. The solution was cooled to −20° C. and treated with 2 ml of 48% aqueous hydrobromic acid under control by HPLC. After 1½ hours at −15 to −20° C. the mixture was neutralized with 20 ml of 2N sodium hydroxide solution and separated in a separating funnel. The organic phase was then washed with saturated sodium bicarbonate solution and thereafter with semi-saturated sodium chloride solution, dried over anhydrous sodium sulphate, filtered and concentrated to about 35 ml. The solution was filtered over a 15 g pad of silica gel [0.04–0.065 mm; solvent: methylene chloride/diethyl ether (3:1)], concentrated somewhat under reduced pressure and continuously replaced by ethanol until finally about 20 mnl of solution remained, from which crystallization set in. The resulting suspension was treated with a small spatula tip of butylated hydroxytoluene and, for isomerization, refluxed for about 16 hours. Then, it was cooled to 0° C., suction filtered and washed with cold ethanol. This gave, after drying at 70° C. under a high vacuum for 2 hours, 3.00 g of dark red crystals which were recrystallized by dissolution in 50 ml of methylene chloride, continuous replacement of the solvent at 40° C./400 mbar (40 kPa) by acetone (finally about 30 ml of liquid), cooling to 0° C., filtration and washing with acetone at −20° C. This gave, after drying at room temperature under a high vacuum for 18 hours, 2.80 g (68% yield, corrected) of astaxanthin as metallic glistening crystals, m.p. 219–220° C.

HPLC content (wt. % compared with standard):
(all E)-astaxanthin: 94%
(9Z+13Z)-astaxanthin: 0.7%
8'-apoastaxanthinal: 1.3%
monomethoxymethyl-astaxanthin: 1.6%
3,3'-dihydroxy-2,3-didehydro-4,4'-diketo-β,β',-carotene ("Halbastacin"): 0.3% methylene chloride: 1%

UV (cyclohexane/3% $CHCl_3$): 476 nm (logE=5.10); mass spectrum: 596 ($M^+$, 10), 147 (100); $^1$H-NMR ($CDCl_3$, 400 MHz): 1.21 and 1.32 (2s, in each case 6H), 1.81 (t, J=12 Hz, 2H), 1.95, 1.99 and 2.00 (3s, 3×6H), 2.16 (dxd, $J_1$=12 Hz, $J_2$=6 Hz, 3.68 (d, J~2 Hz, 2×OH), 4.32 (dxdxd, $J_1$=12 Hz, $J_2$=6 Hz, $J_3$~2 Hz), 6.2–6.7 (div. m, 14 olefinic H).

(b) Hydrolysis and Cleavage in Acetonitrile 4.9 g (about 6.5 mmol) of 4,8,4',8'-tetramethoxy-7,8,7',8'-tetrahydro-3,4,3',4'-bis (O-methylene)-β,β'-carotin (m.p. 167–174° C.) were placed under argon in a 100 ml round flask provided with a magnetic stirrer and argon gasification. 2 ml (3 g, 20 mmol) of 48% aqueous hydrobromic acid were added to the yellow suspension while stirring at −15° C., with the solution immediately becoming dark in color. After 15 minutes the temperature was increased to 0° C. (ice bath) and the suspension was stirred at this temperature for a further 4 hours under HPLC control. Subsequently, the mixture was made basic with 20 ml (20 mmol) of 1N sodium hydroxide solution and suction filtered, and the solid was washed with a large amount of water. The moist crystals were now dissolved in 250 ml of methylene chloride and the solution was dried over anhydrous sodium sulphate, filtered and concentrated to about 50 ml under reduced pressure. The concentrated solution was now filtered over a pad of 15 g of silica gel (0.04–0.065 mm) using a methylene chloride/diethyl ether (3:1) solvent mixture and the filtrate was concentrated somewhat under reduced pressure. Then, 60 ml of ethanol were added thereto continuously and the solution was concentrated until the final volume was about 15–20 ml. For the isomerization, the resulting suspension was now boiled at reflux for 2 hours, cooled to room temperature and filtered, and the crystals were washer with about 10 ml of ethanol at −20° C. Drying at 80° C. under a high vacuum for two hours gave 3.30 g of astaxanthin as dark violet crystals which were recrystallized from 70 ml of methylene chloride and 40 ml of acetone as described under (a). This gave 3.10 g (74% yield) of astaxanthin as deep violet glistening crystals, m.p. 2220° C.;

HPLC content: (wt. % compared with standard):
(all E)-astaxanthin: 91%
(9Z+13Z)-astaxanthin: 0.3%
8'-apoastaxanthinal: 1.7%
monomethoxymethyl-astaxanthin: 1.9%
3,3'-dihydroxy-2,3-didehydro-4,4'-diketo-β,β'-carotene ("Halbastacin"): 3.6% methylene chloride: 1.4%

UV(cyclohexane/3% $CHCl_3$): 477 nm (logE=5.07); mass spectrum and $^1$H-NMR identical with those of an authentic material.

Example 19

Preparation of 3,3'-dihydroxy-4,4'-diketo-β,β'-carotene, i.e., of astaxanthin (formula I wherein $R^1$ is hydroxy and m and n are both 1; "through process" II→III→I)

50 ml of methylene chloride were placed in a 100 ml four-necked sulphonation flask provided with a magnetic stirrer, thermometer and argon gasification and about 55 mg (6 drops, 0.5 mmol) of acetone dimethyl acetal and 40 mg (3 mol %) of anhydrous iron(III) chloride were added. The mixture was stirred at 35–40° C. for 2 hours. It was cooled to −30° C. and 2.80 g (7 mmol) of crocetin dialdehyde dimethyl acetal (HPLC: ≧97% pure) and 3.28 g (18.2 mmol, 2.6 eq.) of 4,6,6-trimethyl-5,6,7,7a-tetrahydro-5-methylidene-1,3-benzodioxol were added thereto in one portion and without solvent. The mixture was stirred at −30° C. to −25° C. for 4½ hours under HPLC control. Then 1 ml (about 1.5 g/9 mmol) of 48% aqueous hydrobromic acid and 50 ml of methylene chloride were added thereto at −25° C. and the mixture was stirred at −15° C. for a further 1¼ hours.

For the neutralization, 5 ml (10 mmol) of 2N sodium hydroxide solution were added to the mixture in one portion and the mixture was stirred for 5 minutes. Then, it was poured into water, the water was separated and the organic phase was washed with saturated sodium bicarbonate solution and semi-saturated sodium chloride solution, dried over anhydrous sodium sulphate and concentrated to about 30 ml under reduced pressure. The concentrated solution was then filtered over a pad of 15 g of silica gel (0.04–0.056 mm) using a methylene chloride/diethyl ether (3:1) solvent mixture, concentrated somewhat under reduced pressure and continuously replaced by ethanol until the final volume was 20 ml, at which point crystallization set in. The resulting suspension was treated with a small spatula tip of butylated hydroxytoluene and, for the isomerization, refluxed for about 16 hours. Then it was cooled to room temperature, suction filtered and washed with cold ethanol. This gave, after drying at 70° C. under a high vacuum for two hours, 3.60 g of violet crystals which were recrystallized twice from methylene chloride/acetone as described under Example 18(a). In this manner there were obtained 3.00 g (68% yield based on crocetin dialdehyde dimethyl acetal used) of astaxanthin as deep violet, glistening crystals, m.p. 219° C.

HPLC content (wt. % compared with standard):

(all E)-astaxanthin: 95%

(9Z+13Z)-astaxanthin: 0.2% monomethoxymethyl-astaxanthin: 1%

8'-apoastaxanthinal: 1%

3,3'-dihydroxy-2,3-didehydro-4,4'-diketo-β,β'-carotene ("halbastacin"): 0.3% methylene chloride: 1%

UV (cyclohexane/3% CHCl$_3$): 476 nm (logE=5.10); mass spectrum and $^1$H-NMR spectrum identical with those of an authentic material.

What is claimed is:

1. A compound of formula III

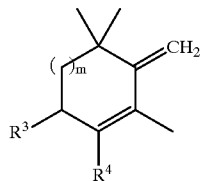

III wherein $R^3$ is hydrogen and $R^4$ is $C_{1-4}$-alkoxy or $R^3$ and $R^4$ together form an optionally substituted methylenedioxy group —O—C($R^5$)($R^6$)—O—, wherein $R^5$ and $R^6$ are each independently hydrogen, $C_{1-4}$-alkyl, or phenyl, and m is 0 or 1.

2. The compound of claim 1, which is selected from the group consisting of 1-isobutoxy-2,4,4-trimethyl-3-exomethylene-cyclopenten, 1-isobutoxy-2,4,4-trimethyl-3-exomethylene-cyclohexene, 2,2,4,6,6-pentamethyl-5,6,7,7a-tetrahydro-5-methylidene-1,3-benzodioxol, and 4,6,6-trimethyl-5,6,7,7a-tetrahydro-5-methylidene-1,3-benzodioxol.

3. The compound of claim 2, which is 1-isobutoxy-2,4,4-trimethyl-3-exomethylene-cyclopentene.

4. The compound of claim 2, which is 1-isobutoxy-2,4,4-trimethyl-3-exomethylene-cyclohexene.

5. The compound of claim 2, which is 2,2,4,6,6-pentamethyl-5,6,7,7a-tetrahydro-5-methylidene-1,3-benzodioxol.

6. The compound of claim 2, which is 4,6,6-trimethyl-5,6,7,7a-tetrahydro-5-methylidene-1,3-benzodioxol.

* * * * *